US008802638B1

(12) United States Patent
Tan et al.

(10) Patent No.: US 8,802,638 B1
(45) Date of Patent: *Aug. 12, 2014

(54) FLAVONOID TREATMENT OF GLYCOGEN SYNTHASE KINASE-BASED DISEASE

(75) Inventors: Jun Tan, Tampa, FL (US); Doug Shytle, Lutz, FL (US); Kavon Rezai-Zadeh, Sherman Oaks, CA (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/421,342

(22) Filed: Apr. 9, 2009

Related U.S. Application Data

(63) Continuation-in-part of application No. 12/020,214, filed on Jan. 25, 2008.

(60) Provisional application No. 60/886,573, filed on Jan. 25, 2007.

(51) Int. Cl.
*C07G 3/00* (2006.01)
*A01N 43/04* (2006.01)
*A61K 31/70* (2006.01)

(52) U.S. Cl.
USPC .............................................. 514/27; 536/6

(58) Field of Classification Search
None
See application file for complete search history.

(56) References Cited

U.S. PATENT DOCUMENTS

2004/0266699 A1  12/2004 Porta
2006/0025337 A1*  2/2006 Sinclair et al. .................. 514/12

FOREIGN PATENT DOCUMENTS

| WO | WO01/49281 A2 | * | 7/2001 |
| WO | 2004013140 A1 | | 2/2004 |
| WO | WO2006/076681 | * | 7/2006 |
| WO | WO2007/005879 | * | 1/2007 |
| WO | WO2007/008548 | * | 1/2007 |

OTHER PUBLICATIONS

Commenges et al., "Intake of Flavonoids and Risk of Dementia," European Journal of Epidemiology, 16(4), 357-363 (Apr. 2000).*
de Rijk et al., "Dietary Antioxidants and Parkinson's Disease," Archives of Neurology, 54(6), 762-765 (Jun. 1997); only abstract supplied.*
Orgogozo et al., "Wine Consumption and Dementia in the Elderly: A Prospective Community Study in the Bordeaux Area," Revue Neurologique, 153(30), 185-192 (Apr. 1997): only abstract supplied.*
Hertog et al. (I), "Content of Potentially Anticarcinogenic Flavonoids of Tea Infusions," Journal Agricultural & Food Chem., 41(8), 1242-1246 (Aug. 1993).*
Hertog et al. (II), "Optimization of Quantitative HPLC Determination of Potentially Anticarcinogenic Flavonoids in Vegetables and Fruits," Journal Agricultural & Food Chem., 40(9), 1591-1598 (Sep. 1992).*
Hertog et al. (III), "Content of Potentially Anticarcinogenic Flavonoids of 28 Vegetables and 9 Fruits Commonly Consumed in the Netherlands," Journal Agricultural & Food Chem., 40(12), 2379-2383 (Dec. 1992).*
Ramassamy, Chas., "Emerging Role of Polyphenolic Compounds in the Treatment of Neurodegenerative Diseases: A Review of Their Intracellular Targets," European Journal of Pharmacology, 545(1), 51-64 (2006): See U.S. Appl. No. 12/020,214 file history for original citation and scanned copy.*
Anon.: "Diosmin (Monograph)," Alternative Medicine Review, 9(3), 308-311 (2004): see U.S. Appl. No. 12/020,214 file history for original citation and scanned copy.*
Rezai-Zadeh et al., "Green Tea Epigallocatechin-3-Gallate (EGCG) Modulates Amyloid Precursor Protein Cleavage and Reduces Cerebral Amyloidosis in Alzheimer Trangenic Mice," The Journal of Neuroscience, 25(38), 8807-8815 (Sep. 21, 2005).*
M. J. O'Neil et al. (eds.), "The Merck Index, 14th Edition," Merck & Co., Whitehouse Station, NJ, 2006, only pp. 558, 807 & 973 supplied (see "Diosmetin," "Diosmin," "Hesperidin," and "Luteolin").*
Wade, L. G., Ch. 23 (Carbohydrates and Nucleic Acids) in "Organic Chemistry, Seventh Edition," Prentice Hall, New York, NY, 2010, only pp. 1097 and 1104-1109 supplied.*
Smith & March, Ch. 2 (Delocalized Chemical Bonding) in "March's Advanced Organic Chemistry, Reactions, Mechanisms, and Structure, Fifth Edition," John Wiley & Sons, New York, NY, 2001, only pp. 32 and 73-77 supplied.*
Beers et al. (eds.), Chapter 158 (Diabetes Mellitus etc.) in The Merck Manual of Diagnosis and Therapy, 18th Edition, Merck & Co., Inc., Rahway, NJ, Jan. 2006, only title pages and text pp. 1274-1294 supplied.*
Beers et al. (eds.), Chapter 221 (Movement and Cerebellar Disorders—Huntington's Disease) in The Merck Manual of Diagnosis and Therapy, 18th Edition, Merck & Co., Inc., Rahway, NJ, Jan. 2006, only title pages and text pp. 1879-1881 supplied.*
Paulo, A., Martins, S., Branco, P., Dias, T., Borges, C., Rodrigues, A. I., Do Ceu Costa, M., Teixeira, A. and Mota-Filipe, H. 2008. "The Opposing Effects of the Flavonoids Isoquercitrin and Sissotrin, Isolated from *Pterospartum tridentatum*, on Oral Glucose Tolerance in Rats." Phytother. Res. vol. 22. pp. 539-543.
Meezan, E., Meezan, E. M., Jones, K., Moore, R., Barnes, S., and Prasain, J. K. 2005. "Contrasting Effects of Puerarin and Daidzin on Glucose Homeostasis in Mice." J. Agric. Food Chem. vol. 53. No. 22. pp. 8760-8767.

(Continued)

*Primary Examiner* — Lawrence E Crane
(74) *Attorney, Agent, or Firm* — Robert J. Varkonyi; Smith & Hopen, P.A.

(57) ABSTRACT

The flavonoid luteolin reduces amyloid-β peptide (Aβ) generation. Luteolin is also a selective GSK-3 inhibitor that 1) decreases amyloidogenic γ-secretase APP processing, and 2) promotes presenilin 1 (PS1) carboxyl-terminal fragment (CTF) phosphorylation. GSK-3α activity is essential for both PS1 CTF phosphorylation states and PS1-APP interaction. These findings were validated in vivo, using a Tg2576 Alzheimer's Disease model system. Luteolin treatment decreased soluble Aβ levels, reduced GSK-3 activity, and disrupted PS1-APP association. In addition, Tg2576 mice treated with diosmin, a glycoside of a flavone structurally and functionally similar to luteolin (diosmetin), displayed significantly reduced Aβ pathology as well.

6 Claims, 45 Drawing Sheets

(56) References Cited

OTHER PUBLICATIONS

Balasubramanian, S., Zhu, L., and Eckert, R. L. 2006. "Apigenin Inhibition of Involucrin Gene Expression is Associated with a Specific Reduction in Phosphorylation of Protein Kinase C delta Tyr311." The Journal of Biological Chemistry. vol. 281. No. 47. pp. 36162-36172.

Vlachopoulos, C., Alexopoulos, N., Dima, I., Aznaouridis, K., Andreadou, I., and Stefanadis, C. 2006. "Acute Effect of Black and Green Tea on Aortic Stiffness and Wave Reflections." Journal of the American College of Nutrition. vol. 25. No. 3. pp. 216-223.

Wang, F., Zeltwanger, S., Yang, I. C.-H., Nairn, A. C., and Hwang, T. 1998. "Actions of Genistein on Cystic Fibrosis Transmembrane Conductance Regulator Channel Gating." J. Gen. Physiol. vol. 111. pp. 477-490.

Liew, R., Williams, J. K., Collins, P., and Macleod, K. T. 2003. "Soy-Derived Isoflavones Exert Opposing Actions on Guinea Pig Ventricular Myocytes." The Journal of Pharmacology and Experimental Therapeutics. vol. 304. No. 3. pp. 985-993.

Duff et al. 2004. "Transgenic Mouse Models of Alzheimer's Disease: How Useful Have They Been for Therapeutic Development?" Briefings in Functional Genomics and Proteomics. vol. 3 No. 1. pp. 47-59.

Mineur et al. 2005. "Genetic Mouse Models of Alzheimer's Disease." Neural Plasticity. vol. 12. No. 4. pp. 299-310.

The Free Online Dictionary. 2011. "Concurrently." Accessed on Dec. 15, 2011. http://www.thefreedictionary.com/concurrently.

Merriam-Webster. 2011. "Concurrent." Accessed on Dec. 15, 2011. http://merriam-webster.com/dictionary/concurrent.

Doble et al. 2003. "GSK-3: Tricks of the Trade for a Multi-Tasking Kinase." Journal of Cell Science. vol. 116. pp. 1175-1186.

Engel et al. 2006. "Full Reversal of Alzheimer's Disease-Like Phenotype in a Mouse Model with Conditional Overexpression of Glycogen Synthase Kinase-3." The Journal of Neuroscience. vol. 26. No. 19. pp. 5083-5090.

Farina et al. 2009. "Post-Transcriptional Regulation of Cadherin-11 Expression by GSK-3 and Beta-Catenin in Prostate and Breast Cancer Cells." Plos One. vol. 4. Issue 3. pp. 1-9.

Jope et al. 2007. Glycogen Synthase Kinase-3 (GSK3): Inflammation, Diseases, and Therapeutics. Neurochem. Res. vol. 32. No. 4-5. pp. 577-595.

Lei et al. 2011. "GSK-3 in Neurodegenerative Diseases." International Journal of Alzheimer's Disease. vol. 2011. Article ID. 189246. pp. 1-9.

McGowan et al. 2000. "Amyloid-Like Inclusions in Huntington's Disease." Neuroscience. vol. 100. No. 4. Abstract.

Mussmann et al. 2007. "Inhibition of GSK3 Promotes Replication and Survival of Pancreatic Beta Cells." Journal of Biological Chemistry. vol. 282. No. 16. pp. 12030-12037.

Pubchem Compound. 2006. "CID 10429217—Compound Summary." Accessed on Dec. 21, 2011. http://pubchem.ncbi.nlm.nih.gov/summary.cgi?cid=10429217&loc=ec_rcs.

Pubchem Compound. 2007. "XSKVALGSZYJVNT-UHFF-FAOYSA-N—Compound Summary." Accessed on Dec. 21, 2011. http://pubchem.ncbi.nlm.nih.gov/summary.cgi?cid=158141159 &loc=ec_rcs.

Wang et al. 2010. "Identification of Novel 1,4-Benzoxazine Compounds that are Protective in Tissue Culture and in Vivo Models of Neurodegeneration." J. Neurosci. Res. vol. 88. No. 9. pp. 1970-1984.

Rockerfeller, "U-Amaloid". Accessed on Jun. 20, 2011, http://sakmarlab.com/WhatWeDo/AmyloidDisease/.

Chaoyun Li, et al., Drug pipeline in neurodegeneration based on transgenic mice models of Alzheimer's disease. Ageing Research Reviews, vol. 12, (2013) pp. 116-140.

David B. Ring, et al., Selective Glycogen Synthase Kinase 3 Inhibitors Potentiate Insulin Activation of Glucose Transport and Utilization in Vitro and in Vivo. Diabetes, vol. 52, Mar. 2003, pp. 588-595.

Rlh Bigelow, et al., Figure 1: The green tea catechins, (-)-Epigallocatechin-3-gallate (EGCG) and (-)-Epicatechin3-gallate (EGCG), inhibit HGF/Met signaling in immortalized and tumorigenic breast epithelial cells. http://www.nature.com/onc/journal/v25/n13/fig_tab/1209227f1.html. Accessed on Apr. 9, 2013.

\* cited by examiner

Tg2576/Luteolin

20 X

Tg2576/Luteolin

20 X

FLAVONOID TREATMENT OF GLYCOGEN SYNTHASE KINASE-BASED DISEASE

CROSS REFERENCE TO RELATED APPLICATION

This application is a continuation-in-part of co-pending U.S. patent application Ser. No. 12/020,214, entitled "Treatment of Glycogen Synthase Kinase-Based Disease", filed on Jan. 25, 2008, which claims priority to U.S. Provisional Patent Application No. 60/886,573, entitled "Glycogen Synthase Kinase-3/Gamma Secretase Inhibitors", filed Jan. 25, 2007. The contents of which are herein incorporated by reference.

FIELD OF INVENTION

This invention relates to enzyme inhibitors. Specifically, the invention relates to inhibitors of amyloid peptide processing enzymes and treatments of Alzheimer's disease.

BACKGROUND OF THE INVENTION

Alzheimer's disease (AD) is a widespread cognitive disease characterized by neurodegeneration, agglomeration of β-Amyloid (Aβ) protein plaques around neurons and within cerebral vasculature, and neurofibrilliary tangles in the brain. Extensive studies indicate Aβ peptide generation and plaque aggregation are key pathological events in the development of AD. The studies evidence Aβ peptides are neurotoxic, as they are reported mediators of apoptosis, inflammation, and oxidative stress. For this reason, some of the earliest proposed therapeutic strategies entail the prevention or elimination of these Aβ peptides and subsequent deposits.

Aβ peptides are produced via the amyloidogenic pathway of amyloid precursor protein (APP) proteolysis, which involves the concerted effort of β and γ-secretases. Initially, β-secretase (BACE) cleaves APP, creating an Aβ-containing carboxyl-terminal fragment known as β-C-terminal fragment (β-CTF), or C99 and an amino-terminal, soluble APP-β (sAPP-β) fragment, which is released extracellularly. Intracellularly, the β-CTF fragment is then cleaved by a multiprotein γ-secretase complex, resulting in generation of the Aβ peptide and a smaller γ-CTF, also known as C57. While both cleavage events are essential to the formation of the peptide, it is the γ-secretase cleavage that determines which of the two major forms of the peptide ($A\beta_{1-40, 42}$) will be generated and, consequently, the peptide's ability to aggregate and the rate at which it is deposited. Thus, one clear potential therapeutic target for AD has been γ-secretase.

Notch signaling pathways are important in cellular development and dysregulation is linked to tumorigenesis. Intracellular γ-secretase processes Notch pathway receptors. Despite the potential toxicity involving possible disruption of Notch signaling and intracellular accumulation of β-CTFs, γ-secretase inhibition remains a viable anti-amyloidogenic strategy. Novel γ-secretase inhibitors (GSI) significantly reduce Aβ production both in vitro and in vivo, initial testing of GSIs has indicated the GSIs improve cognitive functioning in a transgenic mouse model of AD (Tg2576). These finding have functioned to further the vigorous search for potential candidate GSIs. Glycogen synthase kinase 3 (GSK-3) is a tonically active serine/threonine kinase, which has been implicated in several disorders of the CNS. With regard to AD, both isoforms of GSK-3 (α and β) have been found to directly phosphorylate tau on residues specific to hyperphosphorylated paired helical filaments (PHFs), GSK-3β has been shown to phosphorylate APP and to contribute to Aβ mediated neurotoxicity, and GSK-3β has been found to phosphorylate PS1, which may act as a docking site for subsequent tau phosphorylation. Therefore, GSK-3 inhibitors are especially attractive as they may not only oppose Aβ generation but also neurofibrillary tangle (NFT) formation. Moreover, Phiel and colleagues (2003) reported that inhibition of the GSK-3α isoform may regulate γ-secretase cleavage of APP in a substrate-specific manner. Accordingly, this selective inhibition of GSK-3 might provide the maximal therapeutic benefit while reducing the potential for toxic side-effects.

SUMMARY OF THE INVENTION

In one embodiment, flavonoids were found to selectively inhibit GSK-3 activity, thereby promoting PS1 phosphorylation, which consequently inactivates gamma secretase. Flavonoids within the flavone family, including luteolin, disomin, and diosmetin were found to effectively inhibit GSK-3, and very effectively inhibit GSK-3α. Luteolin was found to attenuate Aβ generation and to possess the ability to protect against the multiple arms of AD pathology. Luteolin, categorized as a citrus bioflavonoid, has been previously shown to be a potent free radical scavenger, anti-inflammatory agent, and immunomodulator. Treatment of both murine N2a cells transfected with the human "Swedish" mutant form of APP (Swe-APP N2a cells) and primary neuronal cells derived from Alzheimer's "Swedish" mutant APP overexpressing mice (Tg2576 line) with luteolin resulted in a significant reduction in Aβ generation. Data show that luteolin treatment achieved this reduction through selective inactivation of the GSK-3α isoform, which decreases amyloidogenic γ-secretase APP processing, and promotes presenilin-1 carboxyl-terminal fragment (PS1-CTF) phosphorylation. GSK-3α activity is essential for both PS1-CTF phosphorylation regulation and PS1-APP interaction. Deregulation of presenilin 1 (PS1) phosphorylation, which forms the catalytic core of the γ-secretase complex, allows PS1-CTF levels to increase or continue in unregulated and results in loss of gamma secretase activity, which further results in decreased production of Aβ (toxic peptide). As in vivo validation, administration of luteolin to Tg2576 mice similarly reduced Aβ generation through GSK-3 inhibition. Further, flavonoid administration disrupts PS1-APP association and impacts PS1 phosphorylation-dependent regulation of amyloidogenesis.

In another embodiment, flavonoids within the flavone family, including luteolin, disomin, and diosmetin were found to efficiently inhibit proper association of the secretase complex with its substrate, through increased phosphorylation of PS1, preventing APP processing. The flavones used in the present invention possess a common backbone structure, seen in (I).

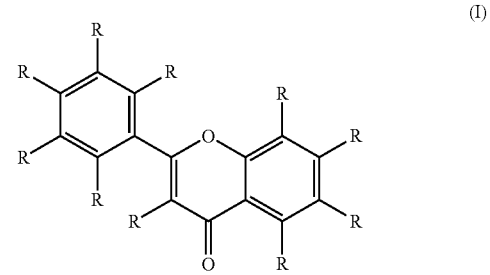

(I)

Many amyloid diseases are characterized by amyloid protein entanglement. In normally functioning brains, tau associates with tubulin thereby stabilizing microtubules. However, when tau becomes hyperphosphorylated, the hyperphosphorylated peptides aggregate into PHFs, which amass in nerve cell bodies NFTs and dystrophic neuritis of amyloid plaques. In another embodiment, flavonoids, especially flavones, inhibit the activity of GSK-3, thereby preventing tau hyperphosphorylation. Preferably, the flavonoids are luteolin, disomin, or diosmetin.

The treatment methods discussed above are effective at treating amyloid diseases and/or diseases involving aberrant GSK-3 activity. The treatments are effective and treating and preventing Alzheimer's disease, Huntington's disease, and type II diabetes.

BRIEF DESCRIPTION OF THE DRAWINGS

For a fuller understanding of the invention, reference should be made to the following detailed description, taken in connection with the accompanying drawings, in which.

Figure 1:
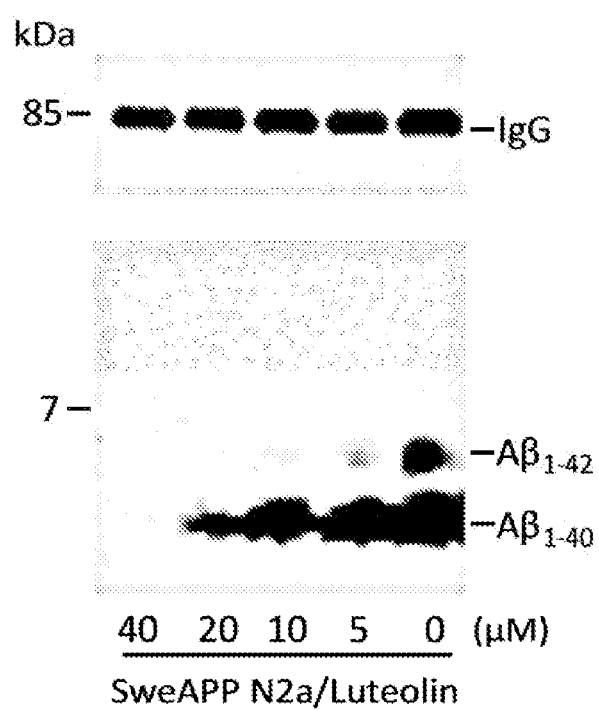
FIG. 1 is a western blot depicting luteolin reducing Aβ generation and decreasing γ-secretase cleavage activity in cultured neuronal cells. SweAPP N2a cells were treated with luteolin at various doses as indicated for 12 hrs. Secreted $A\beta_{1-40, 42}$ peptides were analyzed by immunoprecipitation and Western blot.
Figure 2:
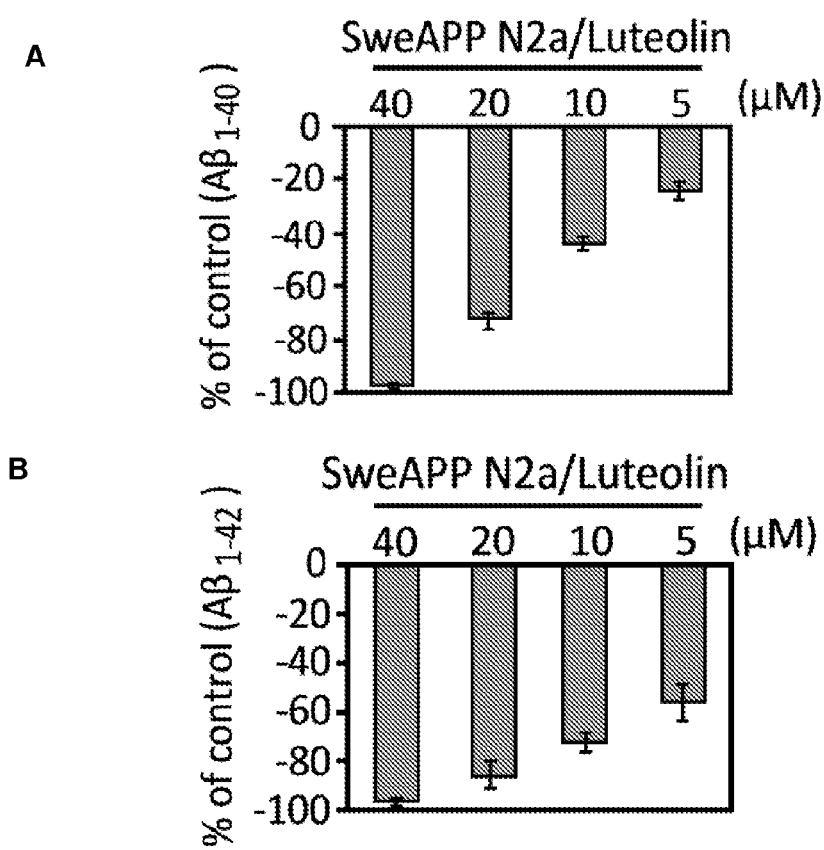
FIG. 2 shows luteolin reduces Aβ generation and decreases γ-secretase cleavage activity in cultured neuronal cells. SweAPP N2a cells were treated with luteolin at various doses as indicated for 12 hrs. Secreted (A) $A\beta_{1-40}$ peptides or (B) $A\beta_{1-42}$ were analyzed by ELISA (left; n=3 for each condition) in conditional media. For Aβ ELISA, data are represented as a percentage of $A\beta_{1-40}$ peptides secreted 12 hrs after luteolin treatment relative to control (untreated).

(b) CID 235240, 2-(3,4-dihydroxyphenyl)-3,6,7-trihydroxy-2,3-dihydrochromen-4-one; (c) CID 24187083, 2-(3,4-dihydroxyphenyl)-3,5,7-trihydroxychromen-4-one; (d) CID 5280417, 2-(3,4-dihydroxyphenyl)-5-hydroxy-3,7-dimethoxychromen-4-one; (e) CID 5280681, 2-(3,4-dihydroxyphenyl)-5,7-dihydroxy-3-methoxychromen-4-one.

FIG. 44(a)-(f) are compound structures of (a) CID 5281604, 2-(3,4-dihydroxyphenyl)-3,7-dihydroxy-5-methoxychromen-4-one; (b) CID 5281612, 5,7-dihydroxy-2-(3-hydroxy-4-methoxyphenyl)chromen-4-one; (c) CID 5281654, 3,5,7-trihydroxy-2-(4-hydroxy-3-methoxyphenyl)chromen-4-one; (d) CID 10018620, 3,5,7-trihydroxy-2-(4-hydroxy-2-methoxyphenyl)chromen-4-one; (e) CID 5281677, 5-hydroxy-2-(4-hydroxy-3-methoxyphenyl)-3,7-dimethoxychromen-4-one; and (f) CID 5281672, 3,5,7-trihydroxy-2-(3,4,5-trihydroxyphenyl)chromen-4-one.

FIG. 45(a)-(f) are compound structures of (a) CID 5281691, 2-(3,4-dihydroxyphenyl)-3,5-dihydroxy-7-methoxychromen-4-one; (b) CID 5281699, 3,5,7-trihydroxy-2-(3-hydroxy-4-methoxyphenyl)chromen-4-one; (c) CID 5318369, 2-(2,6-dimethoxyphenyl)-5-hydroxy-7-methoxychromen-4-one; (d) CID 471, 2-(3,4-dihydroxyphenyl)-3,5,7-trihydroxy-2,3-dihydrochromen-4-one; (e) CID 5320471, 2-(2,6-dihydroxyphenyl)-3,5,7-trihydroxychromen-4-one; and (f) CID 5318626, 2-(3,4-dihydroxyphenyl)-5,7-dihydroxy-8-(3-methylbut-3-enyl)chromen-4-one.

FIG. 46(a)-(f) are compound structures of (a) CID 5381322, 5,7-dihydroxy-2-(2,4,6-trihydroxyphenyl)chromen-4-one; (b) CID 5481961, 2-(2,4-dihydroxyphenyl)-5,7-dihydroxy-3-(3-methylbut-2-enyl)chromen-4-one; (c) CID 5482937, [2-(3,4-dihydroxyphenyl)-5,7-dihydroxy-4-oxochromen-3- yl] acetate; (d) CID 5488211, 2-(2,4-dimethoxyphenyl)-5,7-dihydroxychromen-4-one; (e) CID 5491795, 3,5,7-trihydroxy-2-(2-hydroxy-4-methoxyphenyl)chromen-4-one; and (f) CID 5496476, 5-hydroxy-2-(3-hydroxy-4,5-dimethoxyphenyl)-7-methoxychromen-4-one.

FIG. 47(a)-(e) are compound structures of (a) CID 22718808, 6-[(2E)-3,7-dimethylocta-2,6-dienyl]-5,7-dihydroxy-2-(2,3,4-trihydroxyphenyl)chromen-4-one; (b) CID 9916867, 5-hydroxy-2-(3-hydroxy-4-methoxyphenyl)-7-[(2S,3R,4S,5S,6R)-3,4,5-trihydroxy-6-[[(2S,3R,4R,5R,6S)-3,4,5-trihydroxy-6-methyloxan-2-yl]oxymethyl]oxan-2-yl]oxychromen-4-one; (c) CID 3087722, 5-(2-hydroxyethoxy)-2-(3-hydroxy-4-methoxyphenyl)-7-[(2S,3R,4S,5S,6R)-3,4,5-trihydroxy-6-[[(2R,3R,4R,5R,6S)-3,4,5-trihydroxy-6-methyloxan-2yl]oxymethyl]oxan-2-yl]oxychromen-4-one; (d) CID 5319924, 2-(2,4-dihydroxyphenyl)-5,7-dihydroxy-3,6-bis(3-methylbut-2-enyl)chromen-4-one; (e) 5481958, 2-(2,4-dihydroxyphenyl)-5,7-dihydroxy-3,8-bis(3-methylbut-2-enyl)chromen-4-one;

FIG. 48(a)-(f) are compound structures of (a) CID 10002346, 2-(2,4-dihydroxyphenyl)-5,7-dihydroxy-6,8-bis(3-methylbut-2-enyl)chromen-4-one; (b) CID 21591197, 2-(2,4-dihydroxyphenyl)-6-[(2E)-3,7-dimethylocta-2,6-dienyl]-5,7-dihydroxychromen-4-one; (c) CID 21147600, -[3,4-dihydroxy-5-(3-methylbut-2-enyl)phenyl]-5,7-dihydroxy-8-(3-methylbut-2-enyl)chromen-4-one; (d) CID 6452329, 2-(3,4-dihydroxyphenyl)-3,5-dihydroxy-7-(2-hydroxyethoxy)chromen-4-one; (e) CID 5281670, 2-(2,4-dihydroxyphenyl)-3,5,7-trihydroxychromen-4-one; and (f) CID 10946502, 2-(2,6-dihydroxyphenyl)-5-hydroxy-7-methoxychromen-4-one.

Figure 49:
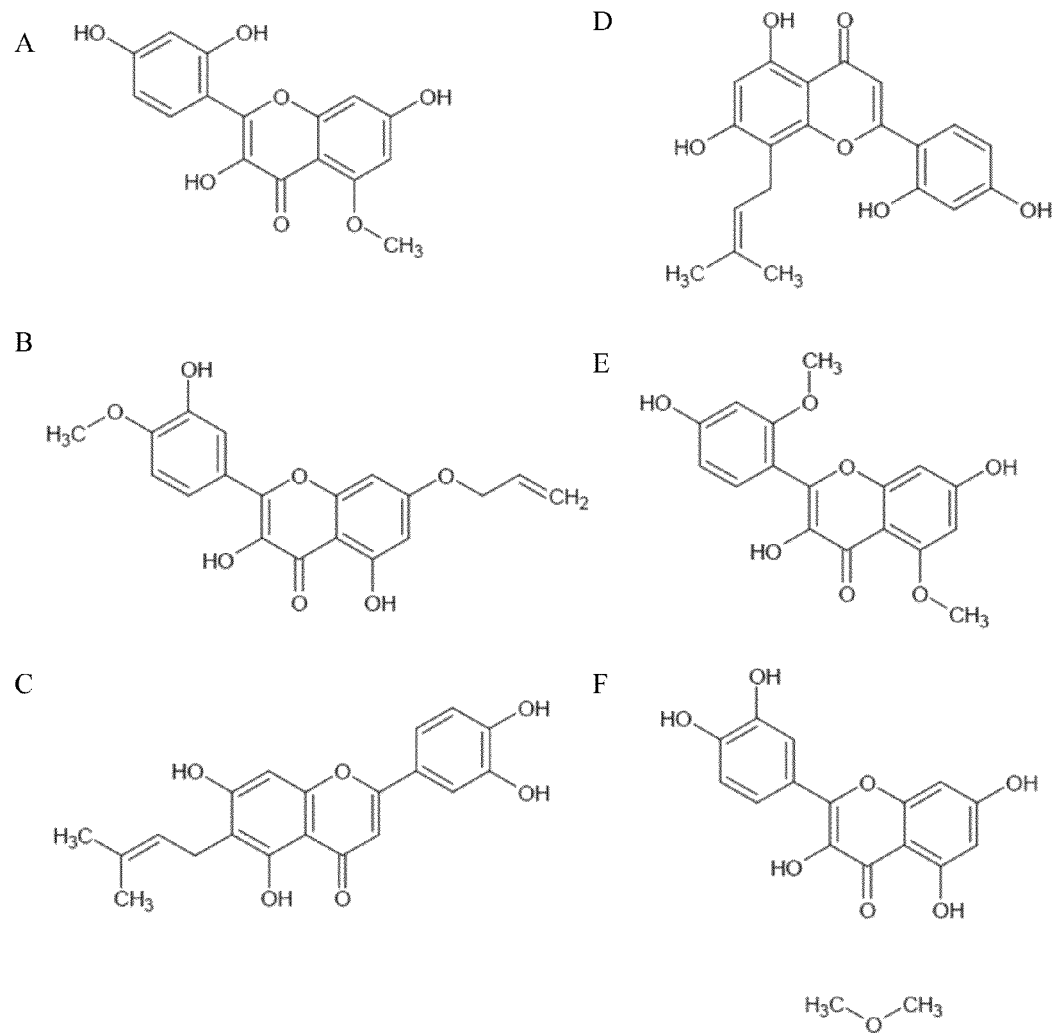
Figure 50:
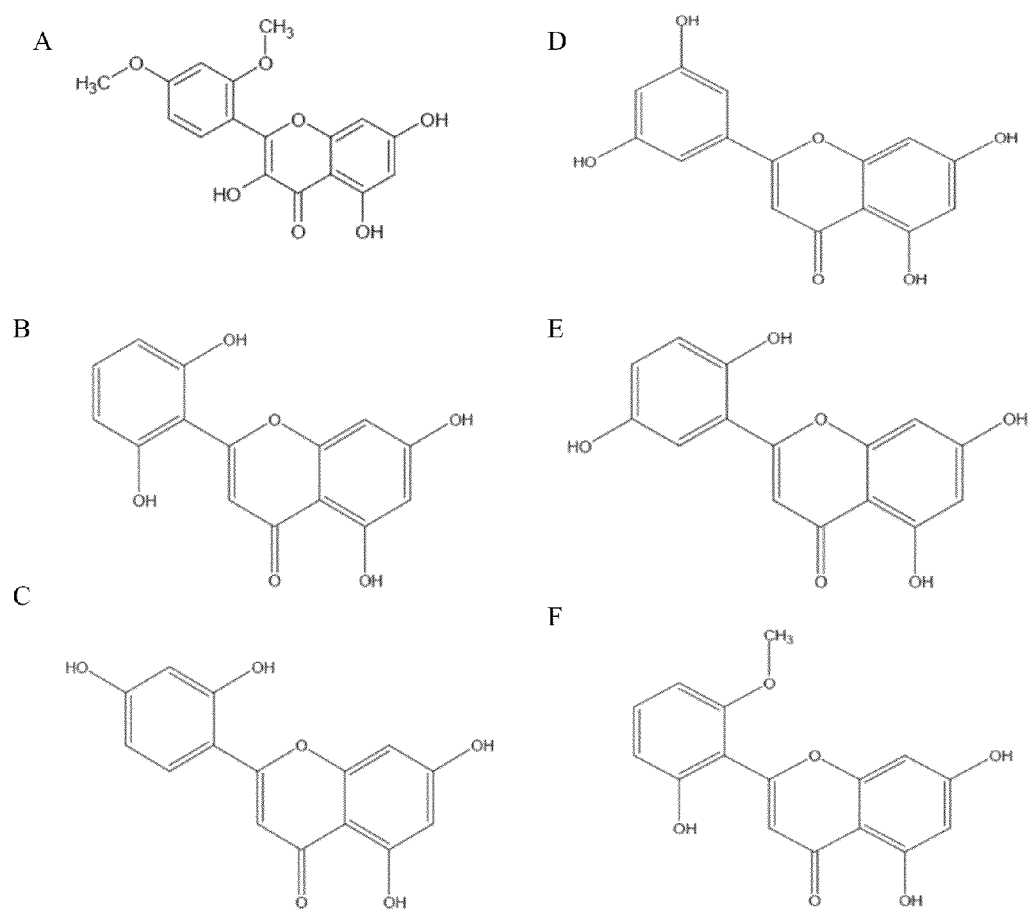
Figure 51:
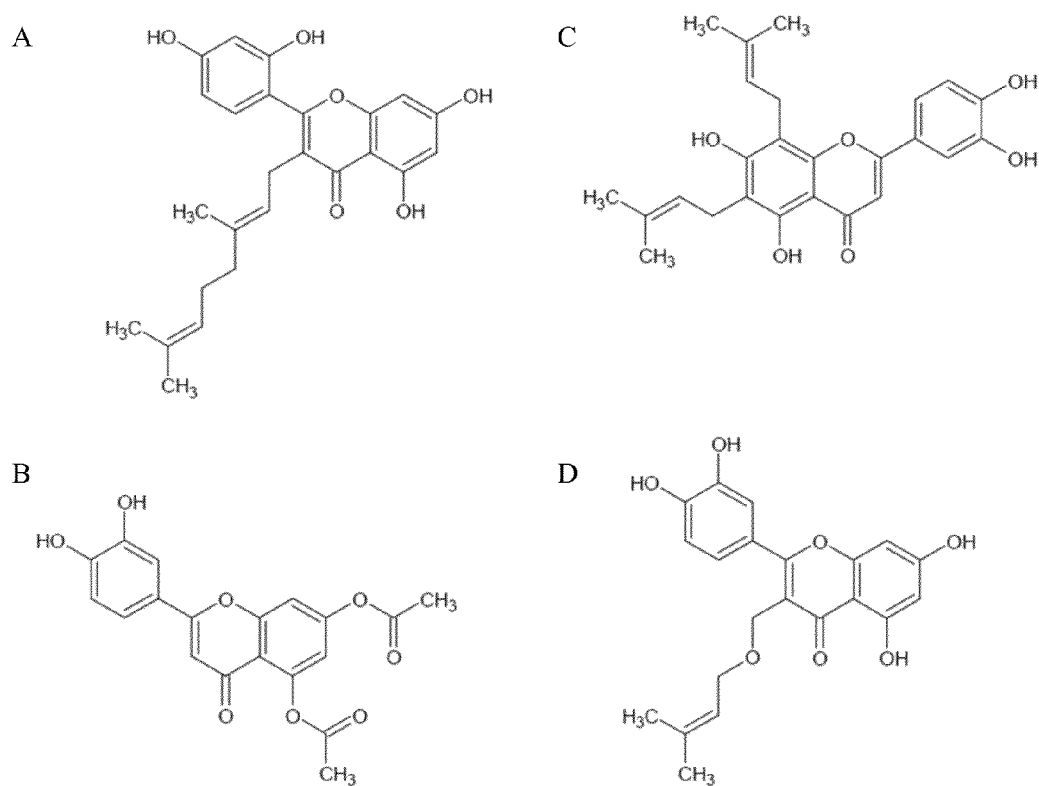
Figure 52:
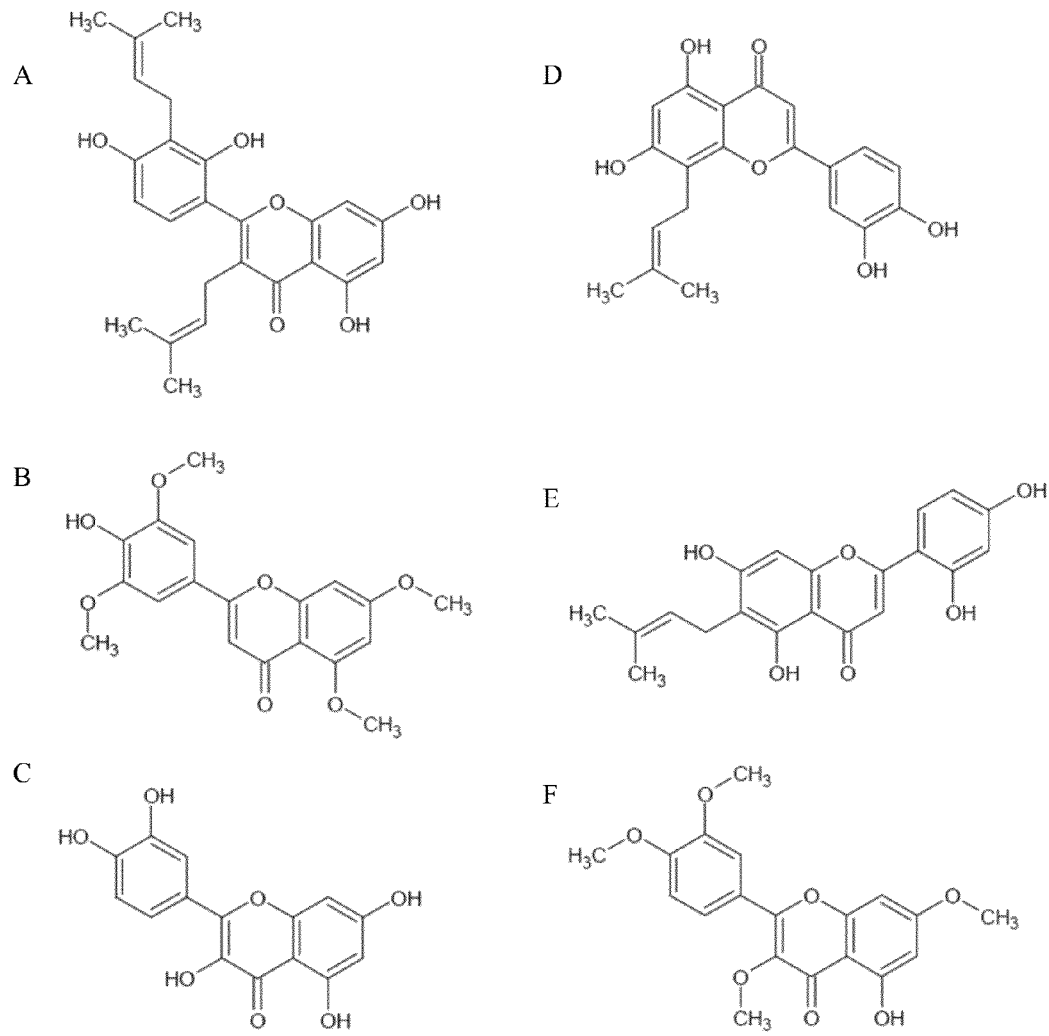
Figure 53:
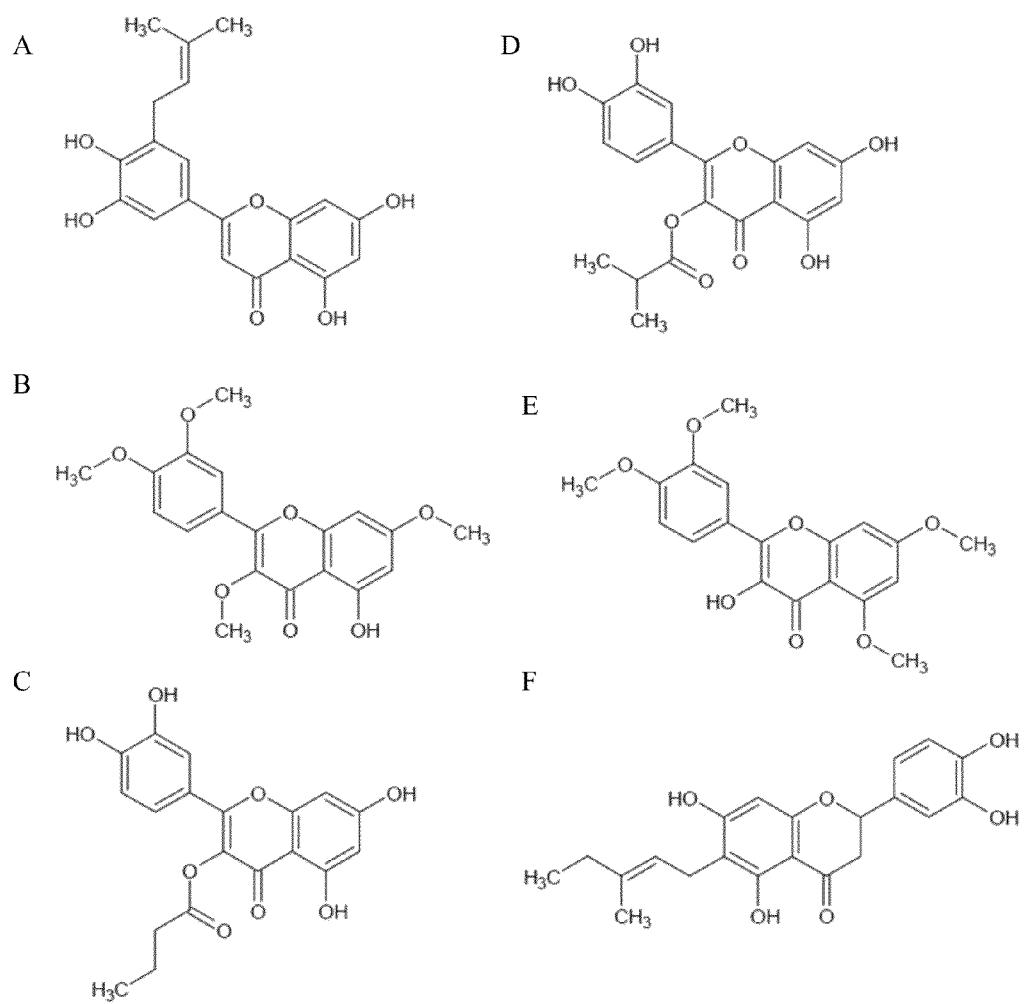

FIG. 49 (a)-(f) are compound structures of (a) CID 11585502, 2-(2,4-dihydroxyphenyl)-3,7-dihydroxy-5-methoxychromen-4-one; (b) CID15814159, 5-hydroxy-2-(3-hydroxy-4-methoxyphenyl)-7-prop-2-enoxychromen-4-one; (c) CID 14604081, 2-(3,4-dihydroxyphenyl)-5,7-dihydroxy-6-(3-methylbut-2-enyl)chromen-4-one; (d) CID 15541482, 2-(2,4-dihydroxyphenyl)-5,7-dihydroxy-8-(3-methylbut-2-enyechromen-4-one; (e) CID 11709692, 3,7-dihydroxy-2-(4-hydroxy-2-methoxyphenyl)-5-methoxychromen-4-one; and (f) CID 20504452, 2-(3,4-dihydroxyphenyl)-3,5,7-trihydroxychromen-4-one; methoxymethane.

FIG. 50(a)-(f) are compound structures of (a) CID 23110081, 2-(2,4-dimethoxyphenyl)-3,5,7-trihydroxychromen-4-one; (b) CID 5321865, 2-(2,6-dihydroxyphenyl)-5,7-dihydroxychromen-4-one (c) CID 5481970, 2-(2,4-dihydroxyphenyl)-5,7-dihydroxychromen-4-one; (d) CID 5487757, 2-(3,5-dihydroxyphenyl)-5,7-dihydroxychromen-4-one; (e) CID 5487756, 2-(2,5-dihydroxyphenyl)-5,7-dihydroxychromen-4-one; and (f) CID 13889369, 5,7-dihydroxy-2-(2-hydroxy-6-methoxyphenyl)chromen-4-one.

FIG. 51(a)-(d) are compound structures of (a) CID 10295791, 2-(2,4-dihydroxyphenyl)-3-[(2E)-3,7-dimethylocta-2,6-dienyl]-5,7-dihydroxychromen-4-one; (b) CID 10429217, [7-acetyloxy-2-(3,4-dihydroxyphenyl)-4-oxochromen-5-yl]acetate; (c) CID 10669924, 2-(3,4-dihydroxyphenyl)-5,7-dihydroxy-6,8-bis(3-methylbut-2-enyl)chromen-4-one; and (d) CID 11474580, 2-(3,4-dihydroxyphenyl)-5,7-dihydroxy-3-(3-methylbut-2-enoxymethyl)chromen-4-one.

FIG. 52(a)-(f) are compound structures of (a) CID 15231527, 2-[2,4-dihydroxy-3-(3-methylbut-2-enyl)phenyl]-5,7-dihydroxy-3-(3-methylbut-2-enyl)chromen-4-one; (b) CID 19595607, 2-(4-hydroxy-3,5-dimethoxyphenyl)-5,7-dimethoxychromen-4-one; (c) CID 5280343, 2-(3,4-dihydroxyphenyl)-3,5,7-trihydroxychromen-4-one; (d) CID 21147597, 2-(3,4-dihydroxyphenyl)-5,7-dihydroxy-8-(3-methylbut-2-enyl)chromen-4-one; (e) CID 399491, 2-(2,4-dihydroxyphenyl)-5,7-dihydroxy-6-(3-methylbut-2-enyl)chromen-4-one; and (f) CID 5352005, 2-(3,4-dimethoxyphenyl)-5-hydroxy-3,7-dimethoxychromen-4-one.

FIG. 53(a)-(f) are compound structures of (a) CID 5315125, 2-[3,4-dihydroxy-5-(3-methylbut-2-enyl)phenyl]-5,7-dihydroxychromen-4-one; (b) CID 462692, 2-(3,4-dimethoxyphenyl)-5-hydroxy-3,7-dimethoxy-2,3-dihydrochromen-4-one; (c) CID 5482938, [2-(3,4-dihydroxyphenyl)-5,7-dihydroxy-4-oxochromen-3-yl] butanoate; (d) CID 5482939, [2-(3,4-dihydroxyphenyl)-5,7-dihydroxy-4-oxochromen-3-yl]2-methylpropanoate; (e) CID 97142, 2-(3,4-dimethoxyphenyl)-3-hydroxy-5,7-dimethoxychromen-4-one; and (f) CID 6450964, 2-(3,4-dihydroxyphenyl)-5,7-dihydroxy-6-[(E)-3-methylpent-2-enyl]chromen-4-one.

Figure 54:
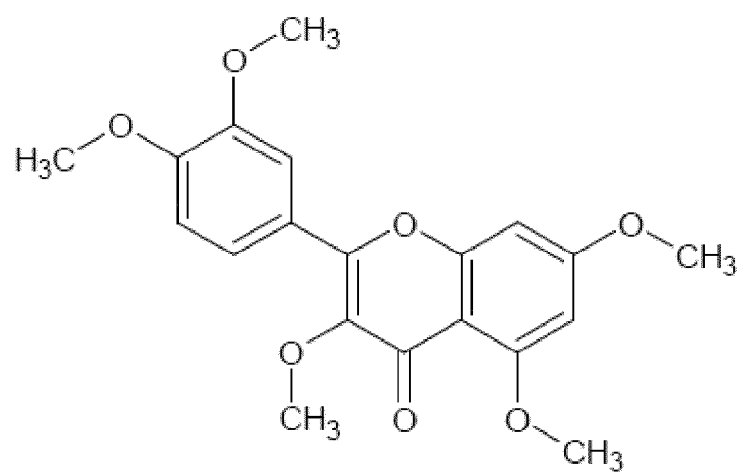

FIG. 54 is a compound structure of CID 97332, 2-(3,4-dimethoxyphenyl)-3,5,7-trimethoxychromen-4-one.

DETAILED DESCRIPTION OF THE PREFERRED EMBODIMENT

"Therapeutically effectve amount" is used to describe concentrations of agents which are effective for producing an intended result, and determined by such considerations as are known in the art. Such results include, for example, inhibition of GSK-3, especially GSK-3α, phosphorylation of PS-1, phosphorylation of PS-1 CTF, inhibition of the GSK-3/PS-1 positive feedback loop, and processing of pro-amyloid proteins, such as APP or β-CTF. The therapeutically effective amount of compound must be effective to achieve a response, including but not limited to total prevention of (e.g., protection against) a disease mediated by GSK-3 and to improved survival rate or more rapid recovery, or improvement or elimination of symptoms associated with neurodegenerative disorders or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. Compositions according to the present invention may be used to inhibit the formation of amyloid proteins and amyloid plaques to produce a favorable change in the brain, or in the disease or condition treated, whether the change is an improvement or cure of the disease or condition. One of skill in the art can readily determine appropriate single dose sizes for systemic administration based on the size of a mammal and the route of administration.

The present invention contemplates administration of the invention to effect a treatment. "Administration" or "administering" is the process by which the compounds of the present invention are administered to a patient in need of treatment. The compounds of the present invention may be administered by numerous methods, including intravenous, intraarterial, intracisternal, intracranial, intraparenchymal (which includes the spinal cord, brain stem, and motor cortex), intracranial, intranigral, intrastriatal, and oral. The compositions may be administered alone or in combination with other compounds. The selected method of administration will vary depending on the disease or condition and patient.

The term term flavonoid refers to plant secondary metabolites and synthetic compounds derived from the flavone backbone. As used herein, the flavone backbone is a 2-phenyl-chromen-4-one (2-phenyl-1,4-benzopyrone) structure. Examples of flavonoids include luteolin, apigenin, tangeritin, chrysin, hydroxyflavone, scutellarein, baicalein, wogonin, disomin, diosmetin, 6,3',4'-trihydroxyflavone, and flavoxate.

Amyloid diseases, such as Alzheimer's disease, Huntington's disease, and type II diabetes, are debilitating diseases resulting from cellularly processed protein agglomerates. Flavonoids were found to selectively inhibit GSK-3 activity, promoting presenilin 1 (PS1) phosphorylation and consequently inactivating gamma secretase. The flavonoids attenuate Aβ generation and possess the ability to protect against the multiple arms of AD pathology. Flavonoids also efficiently inhibit proper association of the γ-secretase complex with its substrate, through increased phosphorylation of PS1, preventing APP processing. In addition, as these flavonoids inhibit the activity of GSK-3, they were capable of preventing tau hyperphosphotrylation.

Sixteen (8♂/8♀) Tg2576 mice (Taconic, Germantown, N.Y.) were used; 8 mice received luteolin, and the other 8 received phosphate buffered saline (PBS). Beginning at 8 months of age, Tg2576 mice were intraperitoneally injected with luteolin (20 mg/kg) or PBS daily for 30 days based on previously described methods. These mice were then sacrificed at 9 months of age for analyses of Aβ levels and Aβ load in the brain according to previously described methods. Animals were housed and maintained in the College of Medicine Animal Facility at the University of South Florida (USF), and all experiments were in compliance with protocols approved by the USF Institutional Animal Care and Use Committee.

Western Blot and Immunoprecipitation

Cultured cells or mouse brain were lysed in ice-cold lysis buffer described above, and an aliquot corresponding to 50 µg of total protein was electrophoretically separated using 12% Tris-HCl or 16.5% Tris-tricine gels. Electrophoresed proteins were then transferred to PVDF membranes, washed in dH$_2$O, and blocked for 1 hr at ambient temperature in Tris-buffered saline (TBS; Bio-Rad) containing 5% (w/v) non-fat dry milk. After blocking, membranes were hybridized for 1 hr at ambient temperature with various primary antibodies. Membranes were then washed 3× for 5 min each in dH$_2$O and incubated for 1 hr at ambient temperature with the appropriate HRP-conjugated secondary antibody (1:1,000). Antibodies were obtained against the amino-terminus and carboxyl-terminus of PS1 (Chemicon, Temecula, Calif.), amino-terminus and carboxyl-terminus of APP (22C11), actin (Roche, Basel, Switzerland), Aβ (6E10, 48G) (Signet Laboratories, Dedham, Mass.), phosphor-GSK3α (ser[21], clone BK202) (Upstate, Lake Placid, N.Y.), phospho-GSK3α/β (pTyr[279/216]) (Sigma), phospho-GSK-3β (Ser[9]) (Sigma) and total GSK-3α/β (Sigma). All antibodies were diluted in TBS containing 5% (w/v) of non-fat dry milk. Blots were developed using the luminol reagent (Pierce Biotechnology). Densitometric analysis was done as previously described using a FluorS Multiimager with Quantity One™ software (39). Immunoprecipitation was performed for detection of sAPP-α, sAPP-β and Aβ by incubating 200 µg of total protein of each sample with various sequential combinations of 6E10 (1:100) and/or 22C11 (1:100) antibodies overnight with gentle rocking at 4° C., and 10 µL of 50% protein A-Sepharose beads were then added to the sample (1:10; Sigma) prior to gentle rocking for an additional 4 hrs at 4° C. Following washes with 1× cell lysis buffer, samples were subjected to Western blot as described above. Antibodies used for Western blot included the APP-carboxyl-terminal antibody (1:50)), amino-terminal APP antibody (clone 22C11), or 6E10 (1:1,000), or actin antibody (1:1,500; as an internal reference control). γ-secretase activity was quantified in cell lysates using available kits based on secretase-specific peptides conjugated to fluorogenic reporter molecules.

ELISA

Cultured cells were lysed in ice-cold-lysis buffer (20 mM Tris, pH 7.5, 150 mM NaCl, 1 mM EDTA, 1 mM EGTA, 1% v/v Triton X-100, 2.5 mM sodium pyropgosphate, 1 mM β-glycerolphosphate, 1 mM Na$_3$VO$_4$, 1 µg/mL leupeptin, 1 mM PMSF). Mouse brains were isolated under sterile conditions on ice and placed in ice-cold lysis buffer. Brains were then sonicated on ice for approximately 3 min, allowed to stand for 15 min at 4° C., and centrifuged at 15,000 rpm for 15 min. Aβ$_{1-40, 42}$ ELISA kits were obtained from IBL-American (Minneapolis, Minn.). Aβ$_{1-40, 42}$ species were detected by acid extraction of brain homogenates in 5 M guanidine buffer, followed by a 1:10 dilution in lysis buffer. Soluble Aβ$_{1-40, 42}$ were directly detected in cultured cell lysates or brain homogenates prepared with lysis buffer described above by a 1:4 or 1:10 dilution, respectively. Aβ$_{1-40, 42}$ was quantified in these samples using the Aβ$_{1-40, 42}$ ELISA kits in accordance with the manufacturer's instructions, except that standards included 0.5 M guanidine buffer in some cases.

Figure 3:
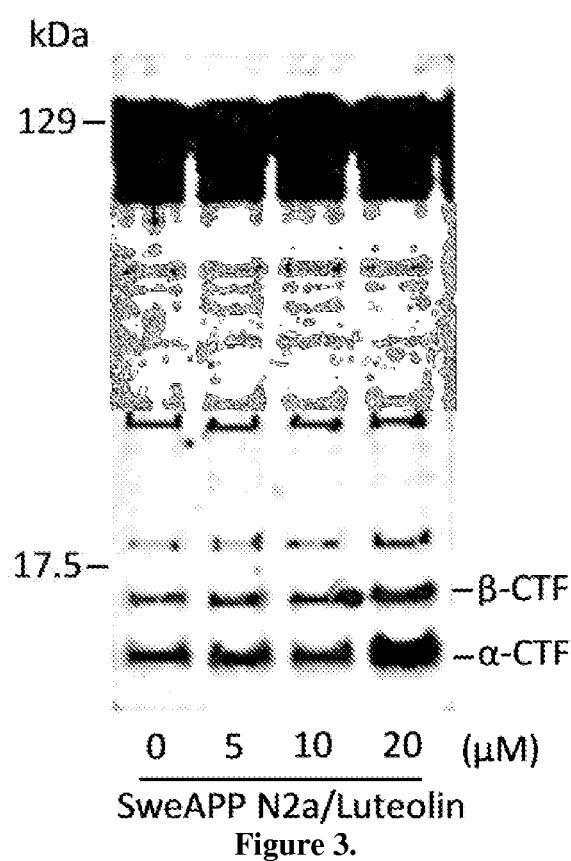
FIG. 3 is a blot showing luteolin reducing Aβ generation and decreasing γ-secretase cleavage activity in cultured neuronal cells. SweAPP N2a cells were treated with luteolin at various doses as indicated for 12 hrs. APP CTFs were analyzed by Western blot in cell lysates and relative fold mean over. One-way ANOVA followed by post hoc comparison revealed significant differences between each dose (P<0.005) except between 20 μM and 40 μM (P>0.05).
Figure 4:
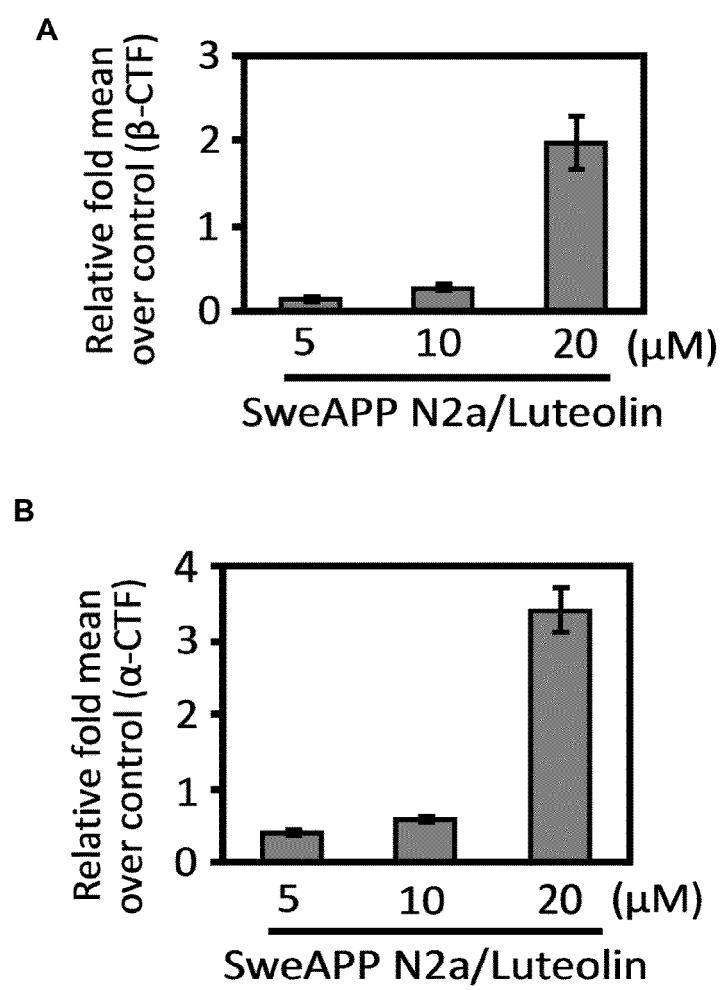
FIG. 4 is a bar graph of the blot in FIG. 3, and depicting luteolin reducing Aβ generation and decreasing γ-secretase cleavage activity in cultured neuronal cells. SweAPP N2a cells were treated with luteolin at various doses as indicated for 12 hrs. The relative fold mean over control for (A) β-CTF and (B) α-CTF was calculated by Densitometry analysis and graphed. One-way ANOVA followed by post hoc comparison revealed significant differences between each dose (P<0.005) except between 20 μM and 40 μM (P>0.05). SweAPP N2a cells were treated with luteolin at a single dose (20 μM) for various time points as indicted.
Figure 5:
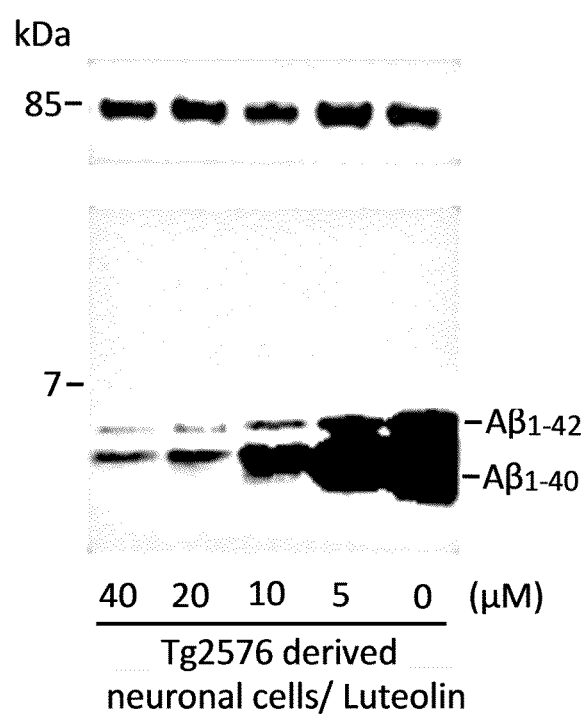
FIG. 5 is a blot depicting luteolin reducing Aβ generation and decreasing γ-secretase cleavage activity in cultured neuronal cells. Tg2576 derived neuronal cells were treated with luteolin at various doses as indicated for 12 hrs. Secreted $A\beta_{1-42}$ peptides were analyzed by immunoprecipitation and Western in conditional media. For Aβ ELISA, data are represented as a percentage of $A\beta_{1-40, 42}$ peptides secreted 12 hrs after luteolin treatment relative to control (untreated).
Figure 6:
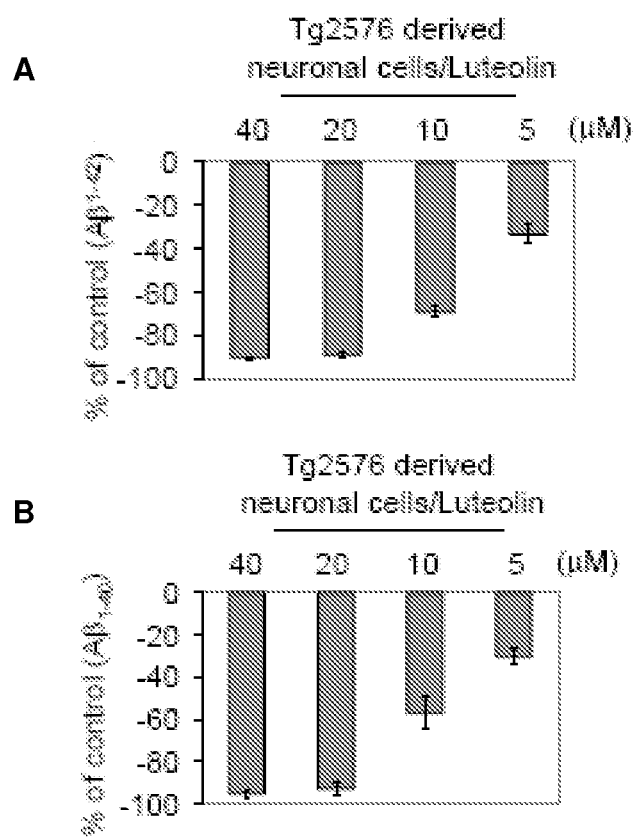
FIG. 6 is a graph of the blot in FIG. 5, and showing luteolin reducing Aβ generation and decreasing γ-secretase cleavage activity in cultured neuronal cells. Tg2576 derived neuronal cells were treated with luteolin at various doses as indicated for 12 hrs. Secreted (A) $A\beta_{1-42}$ or (B) $A\beta_{1-40}$ peptides were analyzed by ELISA (left; n=3 for each condition) in conditional media. For Aβ ELISA, data are represented as a percentage of $A\beta^{1-40, 42}$ peptides secreted 12 hrs after luteolin treatment relative to control (untreated).
Figure 7:
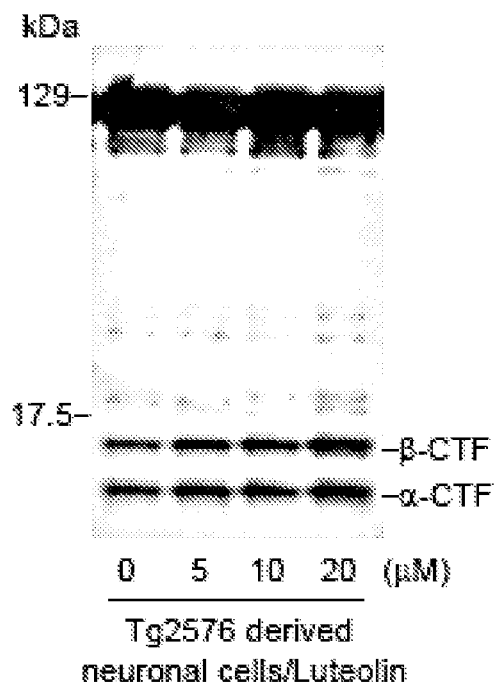
FIG. 7 is a blot showing luteolin reducing Aβ generation and decreasing γ-secretase cleavage activity in cultured neuronal cells. Tg2576 derived neuronal cells were treated with luteolin at various doses as indicated for 12 hrs. APP CTFs were analyzed by Western blot in cell lysates
Figure 8:
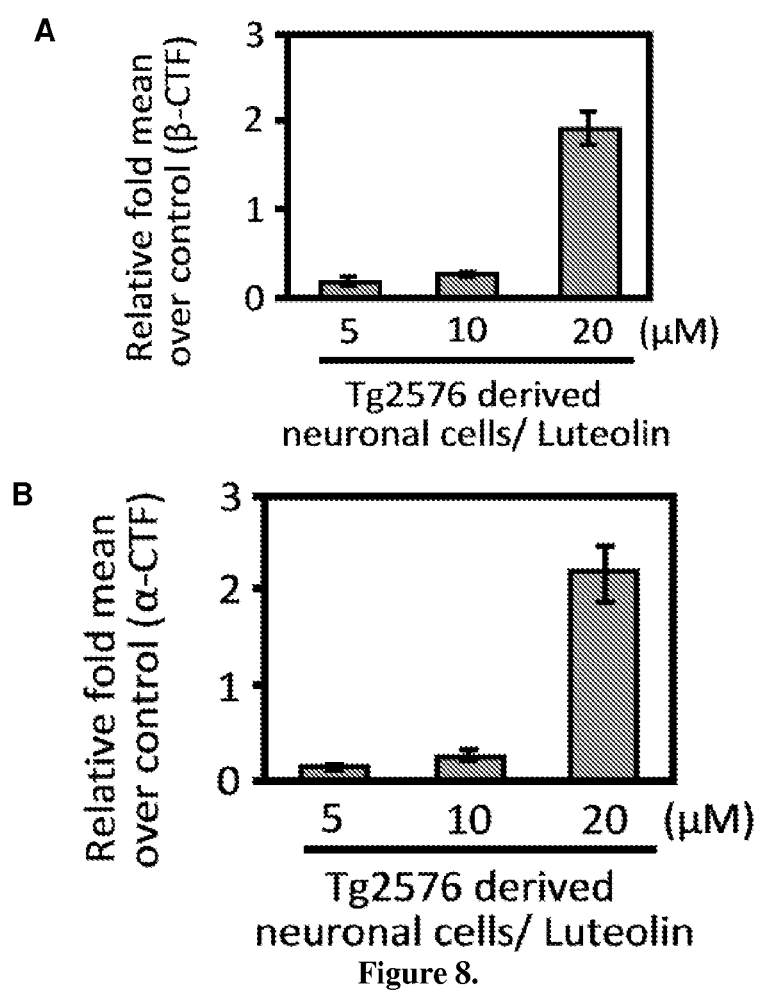
FIG. 8 is a graph of the signal strength of the blot in FIG. 7, and depicting luteolin reducing Aβ generation and decreasing γ-secretase cleavage activity in cultured neuronal cells. Tg2576 derived neuronal cells were treated with luteolin at various doses as indicated for 12 hrs. APP CTFs were analyzed by Western blot and relative fold mean over control (A) β-CTF or (B) α-CTF was calculated by Densitometry analysis. One-way ANOVA followed by post hoc comparison revealed significant differences between each dose (P<0.005) except between 20 μM and 40 μM (P>0.05). SweAPP N2a cells were treated with luteolin at a single dose (20 μM) for various time points as indicted.
Figure 9:
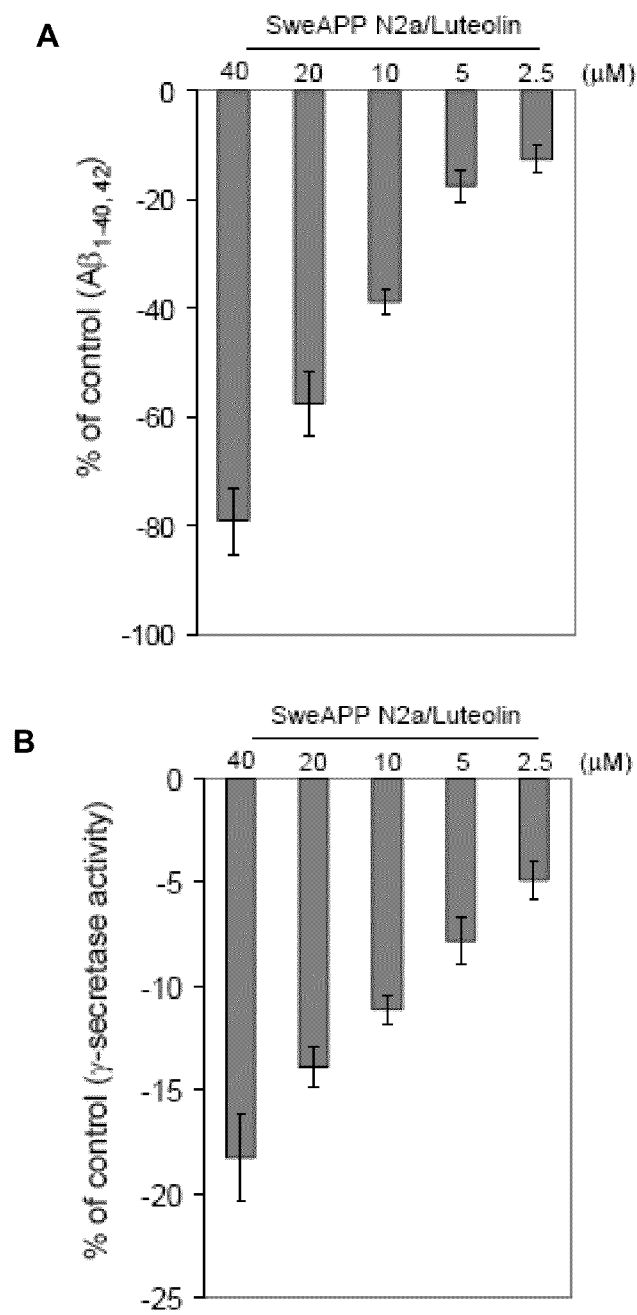
FIG. 9 is a graph of luteolin reducing Aβ generation and decreasing γ-secretase cleavage activity in cultured neuronal cells in a dose dependent manner. (A) Secreted $A\beta^{1-40, 42}$ peptides were analyzed in conditional media by ELISA, (n=3 for each condition). (B) γ-secretase activity was analyzed in cell lysates using secretase cleavage activity assay, (n=3 for each condition). Data was presented as a percentage of fluorescence units/milligrams protein activated 30, 60, 90, 120, 300 min after luteolin treatment relative to control (untreated). A difference was noted between each time point examined (P<0.005). In parallel, a structurally similar compound, apigenin was used as control. However, results were not similar to luteolin (data not shown).
Figure 10:
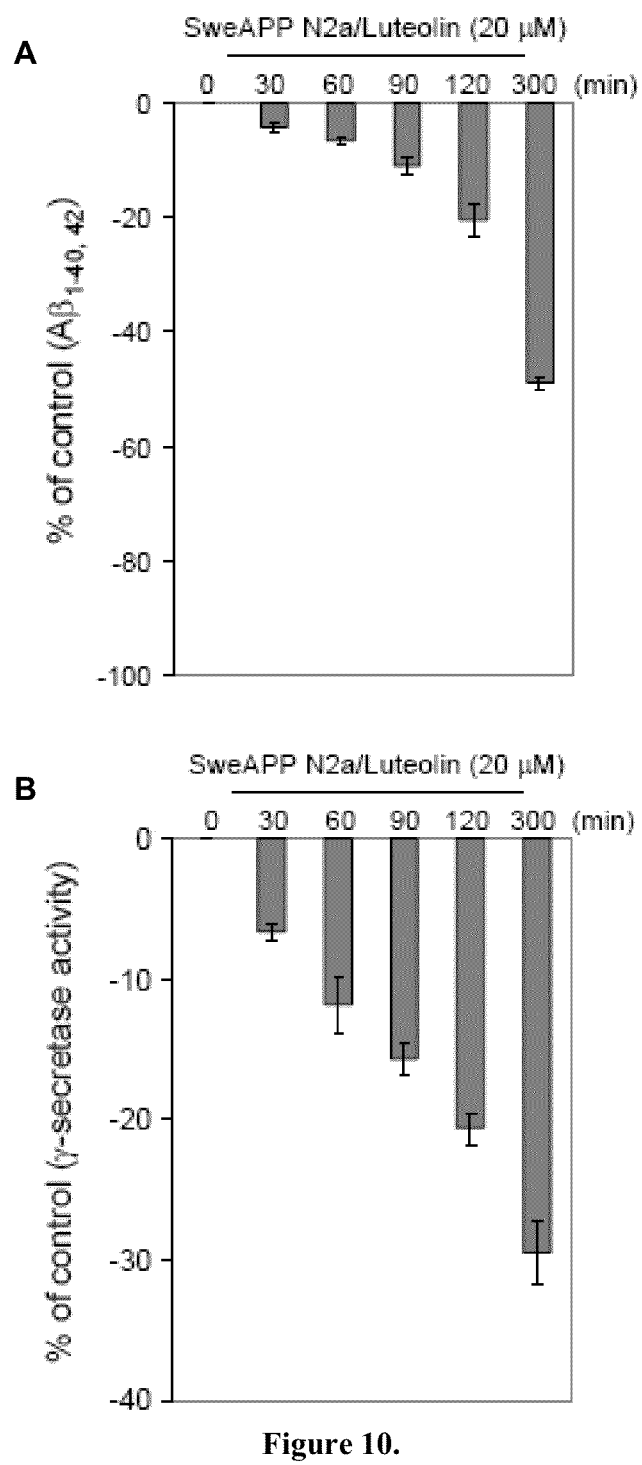
FIG. 10 is a graph showing luteolin reduces Aβ generation and decreases γ-secretase cleavage activity in cultured neuronal cells in a time-dependent manner SweAPP N2a cells were treated with luteolin at a single dose (20 μM) for various time points as indicted. (A) Secreted $A\beta_{1-40, 42}$ peptides were analyzed in conditional media by ELISA, (n=3 for each condition). (B) γ-secretase activity was analyzed in cell lysates using secretase cleavage activity assay, (n=3 for each condition). Data presented as a percentage of fluorescence units/milligrams protein activated 30, 60, 90, 120, 300 min after luteolin treatment relative to control (untreated). A difference was noted between each time point examined (P<0.005). In parallel, a structurally similar compound, apigenin was used as control. However, results were not similar to luteolin (data not shown).
Figure 11:
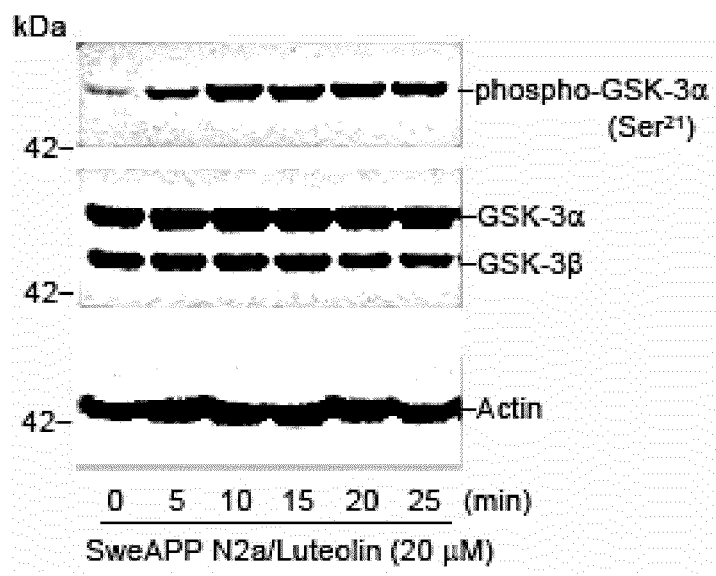
FIG. 11 is a blot showing luteolin selectively inactivates GSK-3α. SweAPP N2a cells were treated with luteolin at 20 μM for various time points as indicated. Cell lysates were prepared and subjected to Western blot analysis in phosphorylated forms of GSK-3α/β. Western blot analysis using anti-phospho-GSK-3α (Ser$^{21}$) antibody shows one band (51 kDa) corresponding to phosphorylated form of GSK-3α or using anti-GSK-3 monoclonal antibody recognizes both total GSK-3α and GSK-3β, 51 and 47 kDa, respectively. Western blot analysis using anti-actin antibody shows actin protein (as an internal reference control). Densitometry analysis shows the ratio of phospho-GSK-3α (Ser$^{21}$) to total GSK-3α as indicated below the figures (n=3 for each condition).
Figure 12:
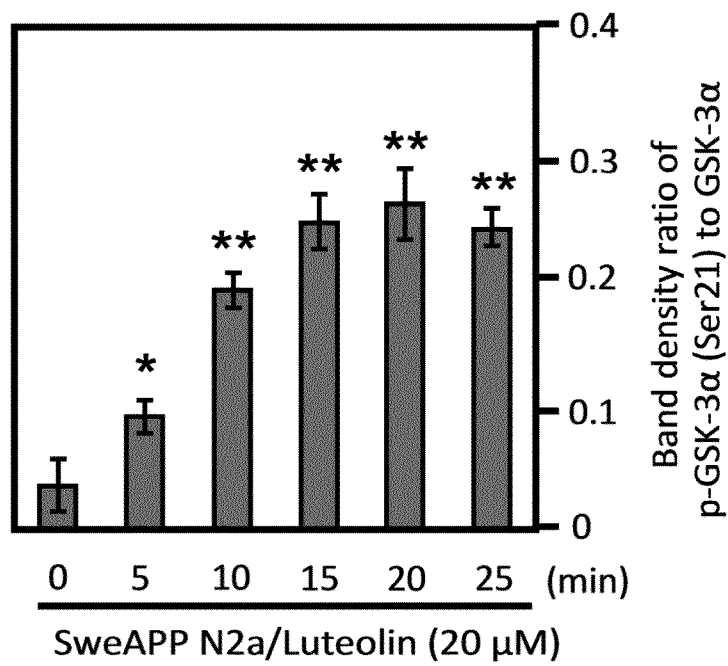
FIG. 12 is a graph of the blot in FIG. 11, and showing signal ratios of p-GSK-3α. SweAPP N2a cells were treated with luteolin at 20 μM for various time points as indicated. Cell lysates were prepared and subjected to Western blot analysis in phosphorylated forms of GSK-3α/β and one-way ANOVA followed by post hoc comparison revealed a significant difference between 0 min and 5, 10, 15, 20 or 25 min (P<0.001). Anti-actin antibody was used as internal reference control.

Luteolin Inhibits Aβ$_{1-40, 42}$ Generation from SweAPP N2a Cells and Tg2576 Mouse-derived Primary Neuronal Cells SweAPP N2a cells and primary neuronal cells derived from Tg2576 mice were treated with varying doses of luteolin to examine luteolin's effect on APP proteolysis. Cellular extracts were collected and analyzed using immunoprecipitation (IP), Western blot, and ELISA. Luteolin (>95% purity by HPLC), (Sigma, St Louis, Miss.), effectively reduced Aβ$_{1-40, 42}$ production in either cell line in a dose dependent manner, shown in FIGS. 1 through 2(B) and 5 through 6(B), and abrogated Aβ$_{1-40, 42}$ peptide generation >70% and >85% at doses of 20 and 40 µM, respectively. See FIGS. 1 through 2(B) and 5 through 6(B). SweAPP N2a and primary Tg2576-derived neuronal cells CTF profiles were analyzed following luteolin treatment to determine at which level luteolin impacts amyloid processing. As illustrated in FIGS. 3 though 4(B) and 7 though 8(B), Western blot analysis shows a dose dependent accumulation of both α and β CTFs, approximately 2-3 fold increases in either cell line.

Due to the implications on γ-secretase activity, luteolin's effect on SweAPP N2a cells was analyzed using a fluorometric assay for γ-cleavage. Luteolin lowered γ-secretase cleavage activity in both a dose and time dependent fashion, depicted in FIGS. 9(A) through 10(B). These dose and time dependent decreases in γ-secretase cleavage activity correlate with decreases in total Aβ generation, seen in FIGS. 9(A) through 10(B), which suggests that luteolin exerts its anti-amyloidogenic effects through down-regulation of γ-secretase activity.

Luteolin Selectively Inactivates GSK-3α/β in SweAPP N2a Cells and Tg2576 Mouse-derived Primary Neuronal Cells The effect luteolin had on a variety of proteins related to and/or required for proper functioning of the γ-secretase complex was evaluated to establish the mechanism whereby luteolin modulates γ-secretase activity and subsequent Aβ generation. Luteolin (20 μM) increased the levels of serine 21-phosphorylated, inactive GSK-3α isoforms in both Swe-APP N2a and primary Tg2576-derived neuronal cells, depicted in FIGS. 12 through 18. However, no significant changes were observed in overall expression of either GSK3-α or β by Western blot, confirming that this phenomenon most likely occurs at the post-translational or protein stage of this kinase. See, FIGS. 12 through 18. This increase in GSK-3α serine 21 residue phosphorylation-mediated inactivation continued through 3 hrs, shown in FIGS. 13 and 17, while the levels of tyrosine 279 phosphorylated active GSK-3α isoforms concurrently decreased in time-dependent manner, shown in FIGS. 13 and 17). More to the point, these time-dependent decreases in phospho-tyrosine 279 active GSK-3α are quite congruent with the increases seen with phospho-serine 21 inactive isoforms. See, FIGS. 12 through 18. FIGS. 14 and 18 indicate abrupt decreases in active phosphorylated isoforms, with concurrent increases in inactive phosphorylated isoforms within 60 minutes of luteolin treatment. Following 2 hours of luteolin treatment, phospho-tyrosine 216 GSK-3β active levels decline. Therefore, luteolin affects GSK-3α/β signaling and confirms that this signaling is a potential upstream event required for modulation of γ-secretase activity. It has been suggested that GSK-3β phosphorylates tau, which ultimately leads to neurofibrillary tangle (NFT) formation. As noted, treatment with luteolin/diosmetin/diosmin results in decreased GSK-3β activity indicating a luteolin/diosmetin/diosmin treatment may be effective in preventing tau activity and NFT formation.

EXAMPLE 1

GSK-3 Inhibition Alters PS1 Processing/Phosphorylation in SweAPP N2a Cells

Cultured cells or mouse brain were lysed in ice-cold lysis buffer described above, and an aliquot corresponding to 50 μg of total protein was electrophoretically separated using 12% Tris-HCl or 16.5% Tris-tricine gels. Electrophoresed proteins were then transferred to PVDF membranes, washed in $dH_2O$, and blocked for 1 hr at ambient temperature in Tris-buffered saline (TBS; Bio-Rad) containing 5% (w/v) non-fat dry milk. After blocking, membranes were hybridized for 1 hr at ambient temperature with various primary antibodies. Membranes were then washed 3× for 5 min each in $dH_2O$ and incubated for 1 hr at ambient temperature with the appropriate HRP-conjugated secondary antibody (1:1,000). All antibodies were diluted in TBS containing 5% (w/v) of non-fat dry milk. Blots were developed using the luminol reagent (Pierce Biotechnology). Densitometric analysis was done as previously described using a FluorS Multiimager with Quantity One™ software. Immunoprecipitation was performed for detection of sAPP-α, sAPP-β and Aβ by incubating 200 μg of total protein of each sample with various sequential combinations of 6E10 (1:100) and/or 22C11 (1:100) antibodies overnight with gentle rocking at 4° C., and 10 μL of 50% protein A-Sepharose beads were then added to the sample (1:10; Sigma) prior to gentle rocking for an additional 4 hrs at 4° C. Following washes with 1× cell lysis buffer, samples were subjected to Western blot as described above. Antibodies used for Western blot included the APP-carboxyl-terminal antibody (1:50)), amino-terminal APP antibody (clone 22C11), or 6E10 (1:1,000), or actin antibody (1:1,500; as an internal reference control). γ-secretase activity was quantified in cell lysates using available kits (R&D Systems, Minneapolis, Minn.), based on secretase-specific peptides conjugated to fluorogenic reporter molecules.

FIGS. 19(A) through 23 depict the Western blot analysis of carboxyl-terminal portions of PS1 reveals three distinct bands. The two bands of highest molecular weight, approximately 20 kD and 18 kD in size, represent phosphorylated PS1 CTFs with a smaller 16 kD band representing the more common CTF product indicative of PS1 endoproteolytic cleavage. Following SweAPP N2a cell treatment with luteolin, PS1 CTF phosphorylation increases. Phospho-PS1 CTF to PS1 CTF ratios differ significantly with luteolin treatment, both dose and time-dependently, depicted in FIG. 19(A) through (C), and correlate with the dose and time-dependent decreases in $A\beta_{1-40, 42}$ generation.

To confirm that the 20 kD and 18 kD bands were phosphorylated PS1 isoforms, SweAPP N2a cells were treated with luteolin (20 μM) prior to lysis and cell lysates incubated with calf intestine alkaline phosphatase (CIAP) (Fermentas, Hanover, Md.), to dephosphorylate any potential phosphorylated proteins, to eliminate skewing of electrophorectic mobilities. Following 30 minutes of incubation, the 20 kD band is not evident in the CIAP treated lysates, seen in FIGS. 21(A) through 22, and the 18 kD band reduced while endogenous CTF, 16 kD, appears to accumulate. When compared to lysates incubated with only reaction buffer, phosphorylated residues decrease in a time dependent manner, shown by the 20 kD CTF:16 kD CTF. See FIGS. 21(A) and (B). While luteolin treatment influenced PS1 CTF species, luteolin had no significant effect on either full-length PS1 or PS1 NTF protein levels. See FIGS. 23(A) and (B). Luteolin affects PS1 phosphorylation and may indicate a means by which γ-secretase activity may be regulated.

To determine if this phenomenon was specifically attributable to luteolin treatment or more generally in regards to GSK-3 inhibition, SweAPP N2a cells were treated with a range of doses of the GSK-3 inhibitor SB-415286 (BIO-MOL®, Plymouth Meeting, Pa.). See FIG. 24(A). Alterations in phospho-PS1 CTF:PS1 CTF ratios were similar to prior experiments and congruent decreases in $A\beta_{1-40, 42}$ generation with SB-415286 treatment were confirmed. FIG. 24(B). GSK-3α and β was successfully knocked-down (>70%, data not shown) with siRNA in SweAPP N2a cells, substantiating the role of GSK-3α in this luteolin-mediated PS1 processing. GSK-3α siRNA transfected cells exhibit significantly higher phosphorylated PS1 isoforms as compared to GSK-3β siRNA or mock transfectants, shown in FIG. 25(A); P<0.001). Similar differences were observed when comparing the level of PS1 phosphorylation in luteolin treated (20 μM) cells to that of GSK-3β siRNA or mock transfectants. See FIG. 25(B); P<0.001), illustrating GSK-3α regulates PS1

CTF phosphorylation and that the 20 kD phospho-PS1 CTF band represents a less active or non-amyloidogenic form of γ-secretase.

EXAMPLE 2

GSK-3α Regulates PS1-APP Association in SweAPP N2a Cells

Figure 26:
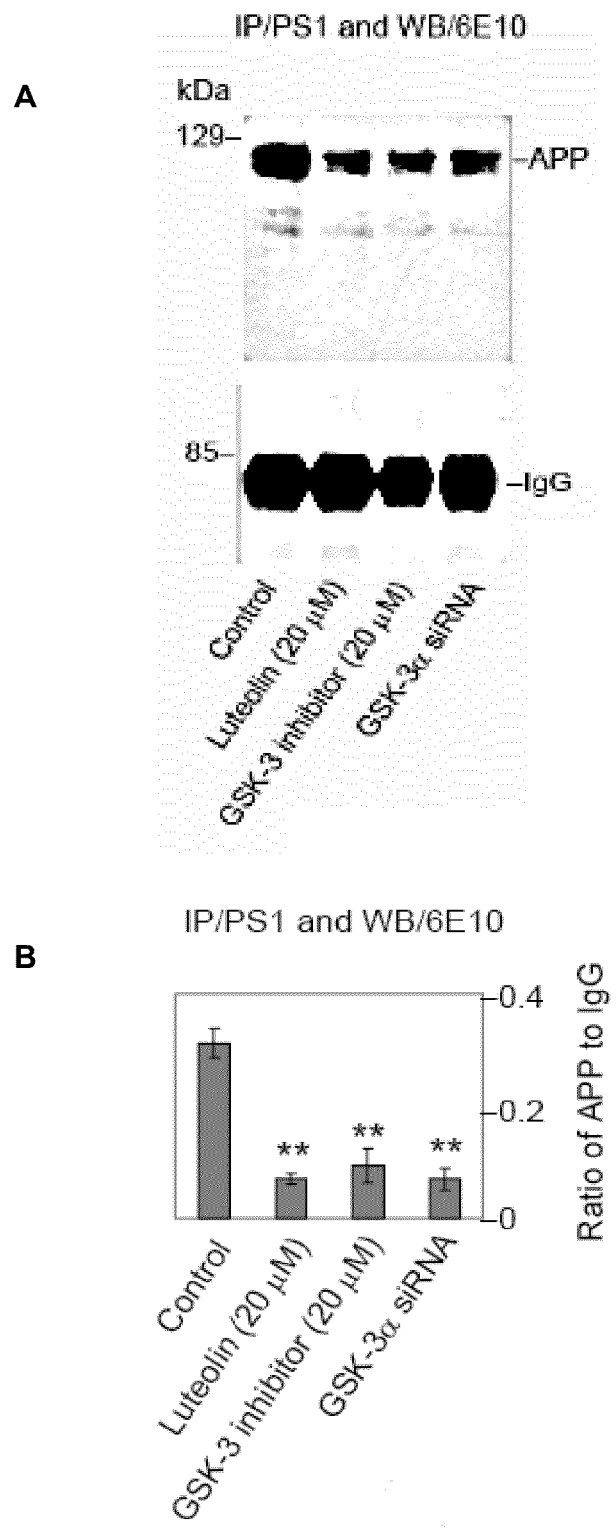
FIG. 26 depicts GSK-3α regulates PS1-APP association. SweAPP N2a cells were treated with either luteolin (20 μm) GSK-3 inhibitor SB-415286 (20 μm) for 4 hrs or transfected with GSK-3α siRNA. (A) Lysates were immunoprecipitated by anti-PS1 CTF antibody and analyzed using Western blot. 6E10 antibodies were used to probe the Western blot. (B) Densitometric analysis of Western blot shows the ratio of APP to IgG as indicated. A t test revealed significant differences between all treatments and control (P<0.001 with n=3 for each condition).
Figure 27:
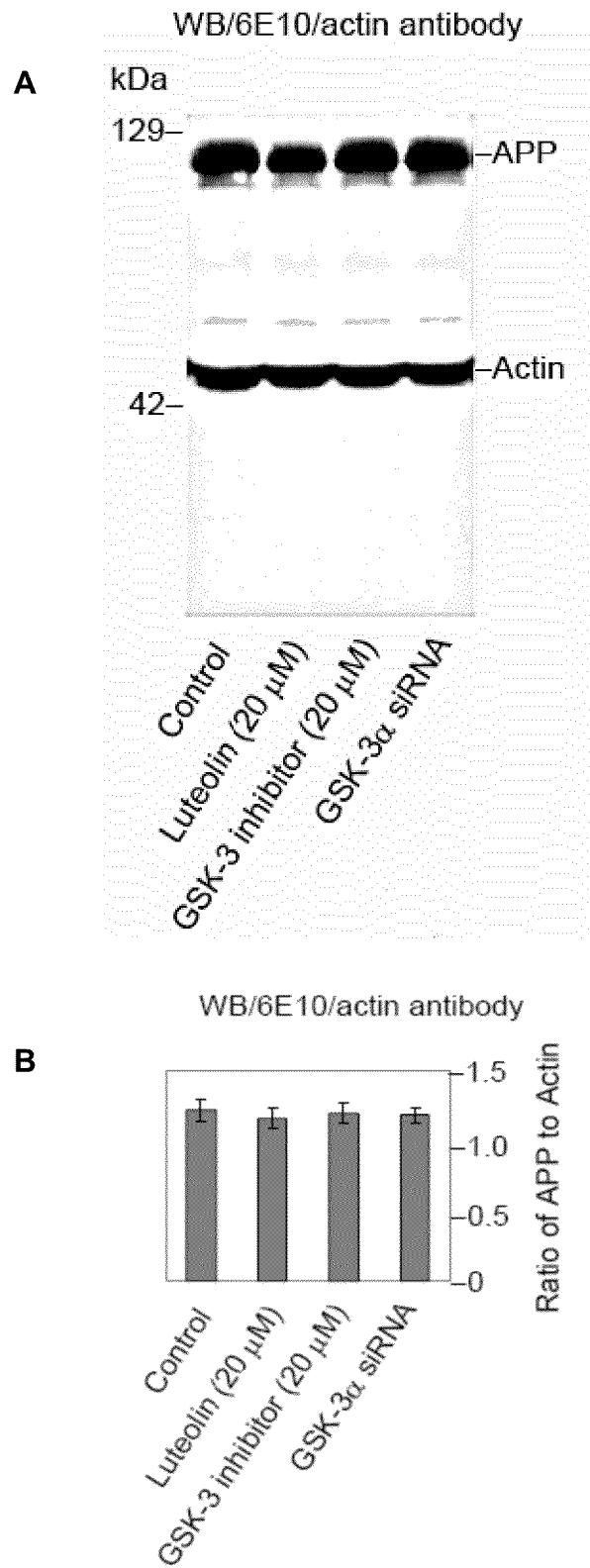
FIG. 27 depicts GSK-3α regulation of PS1-APP association. SweAPP N2a cells were treated with either luteolin (20 μm), GSK-3 inhibitor SB-415286 (20 μm) for 4 hrs, or transfected with GSK-3α siRNA. Cell lysates from these treated cells and GSK-3α siRNA-transfected cells were subsequently analyzed by immunoprecipitation/ Western blot. (A) Cell lysates were analyzed by Western blot by 6E10 antibody. (B) Densitometric analysis of Western blot against anti-actin antibody-stained control reveals no significant changes in the ratio of APP to actin as indicated (P>0.05).

Cell lysates of luteolin-treated SweAPP N2a cells were immunoprecipitated by PS1 antibody and probed for APP to clarify how phospho-PS1 CTF isoforms may regulate γ-secretase activity, seen in FIGS. 26(A) through 27(B). As illustrated in FIGS. 26(A) and (B), the APP-PS1 association is disrupted by luteolin, SB-415286 treatment, and GSK-3α siRNA. This treatment-mediated disruption has no correlation to full-length APP levels, as seen in FIGS. 27(A) and (B), indicating treatment has little effect on APP expression/trafficking. Thus, GSK-3α or, more specifically, downstream phosphorylation of the PS1 CTF plays an essential role in regulating the association of γ-secretase complex with its APP substrate.

EXAMPLE 3

Luteolin Treatment Inhibits GSK-3 Activation and Results in Reduction of Cerebral Aβ Levels in Tg2576 Mice Eight month-old Tg2576 mice were treated with 20 mg/kg luteolin administered by daily intraperitoneal injection for 30 days to validate the above findings in vivo. Mice were anethetized with isofluorane and transcardinally perfused with ice-cold physiological saline containing heparin (10 U/mL). Brains were rapidly isolated and quartered using a mouse brain slicer. The first and second anterior quarters were homogenized for Western blot analysis, and the third and fourth posterior quarters were used for microtome or cryostat sectioning. Brains were then fixed in 4% paraformaldehyde in PBS at 4° C. overnight and routinely processed in paraffin in a core facility at the Department of Pathology (USF College of Medicine). Five coronal sections from each brain (5-μm thickness) were cut with a 150-μm interval. Sections were routinely deparaffinized and hydrated in a graded series of ethanol baths prior to pre-blocking for 30 min at ambient temperature with serum-free protein block. GSK-3α/β immunohistochemical staining was performed using anti-phospho-GSK-3/α/β (pTyr$^{279/216}$) (Sigma, St. Louis, Miss.) antibody (1:50) in conjunction with the VectaStain Elite™ ABC kit coupled with diaminobenzidine substrate. Phospho-GSK-3α/β-positive neuronal cells were examined under bright-field using an Olympus BX-51 microscope.

Figure 28:
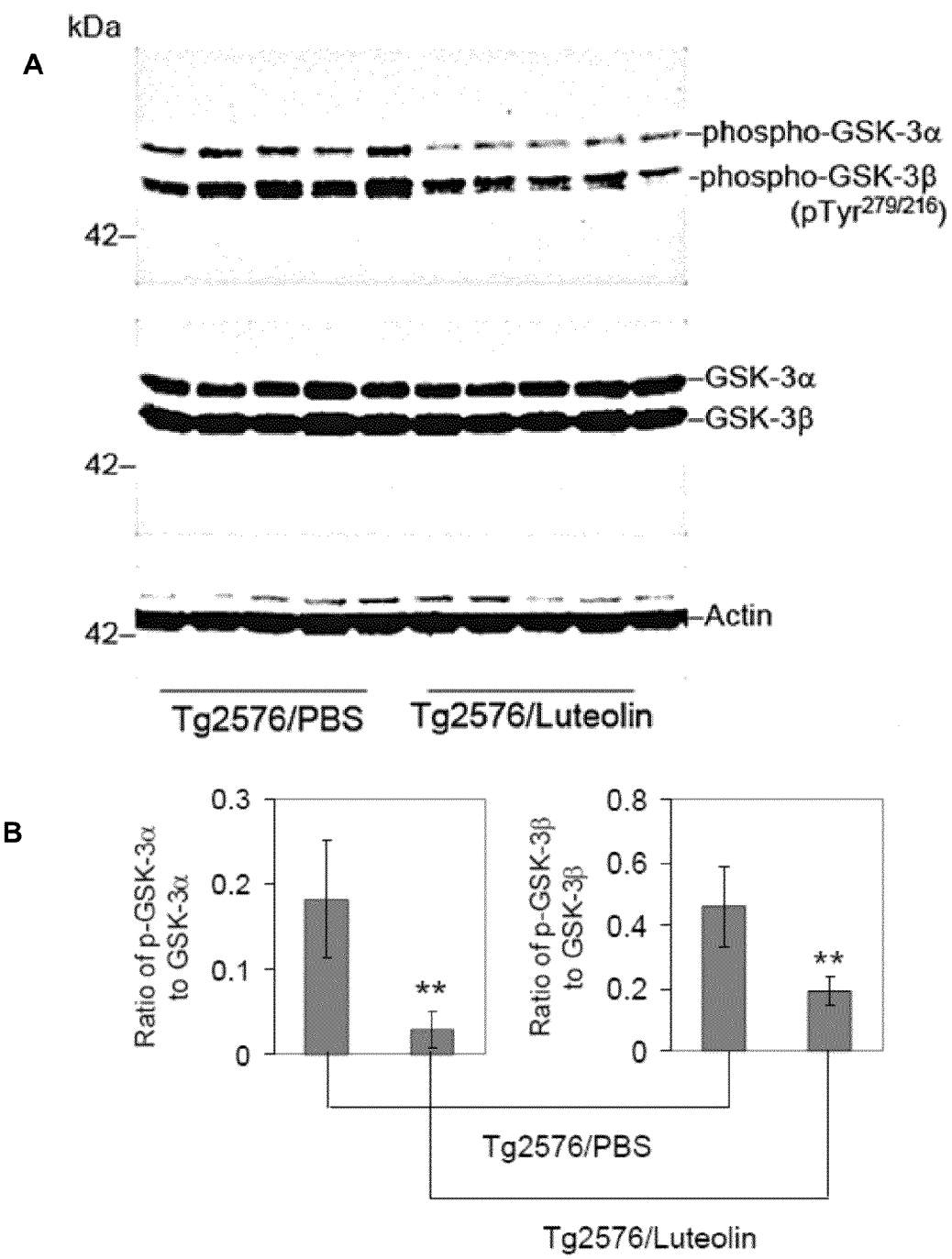
FIG. 28 depicts GSK luteolin inhibiting GSK-3 activation and cerebral amyloidosis in Tg2576 mice. Brain homogenates from Tg2576 mice treated with luteolin (n=5) or vehicle (PBS, n=5) and analyzed. (A) Western blot of brain homogenates with active and holo anti-GSK-3 antibodies with anti-actin antibodies as an internal control. (B) A densitometric graph revealing the ratio of active phosphorylated GSK-3α/β to holo GSK-3. A t test reveals significant reductions in both active GSK-3α and β isoforms from luteolin treated animals compared to control (P<0.001).
Figure 29:
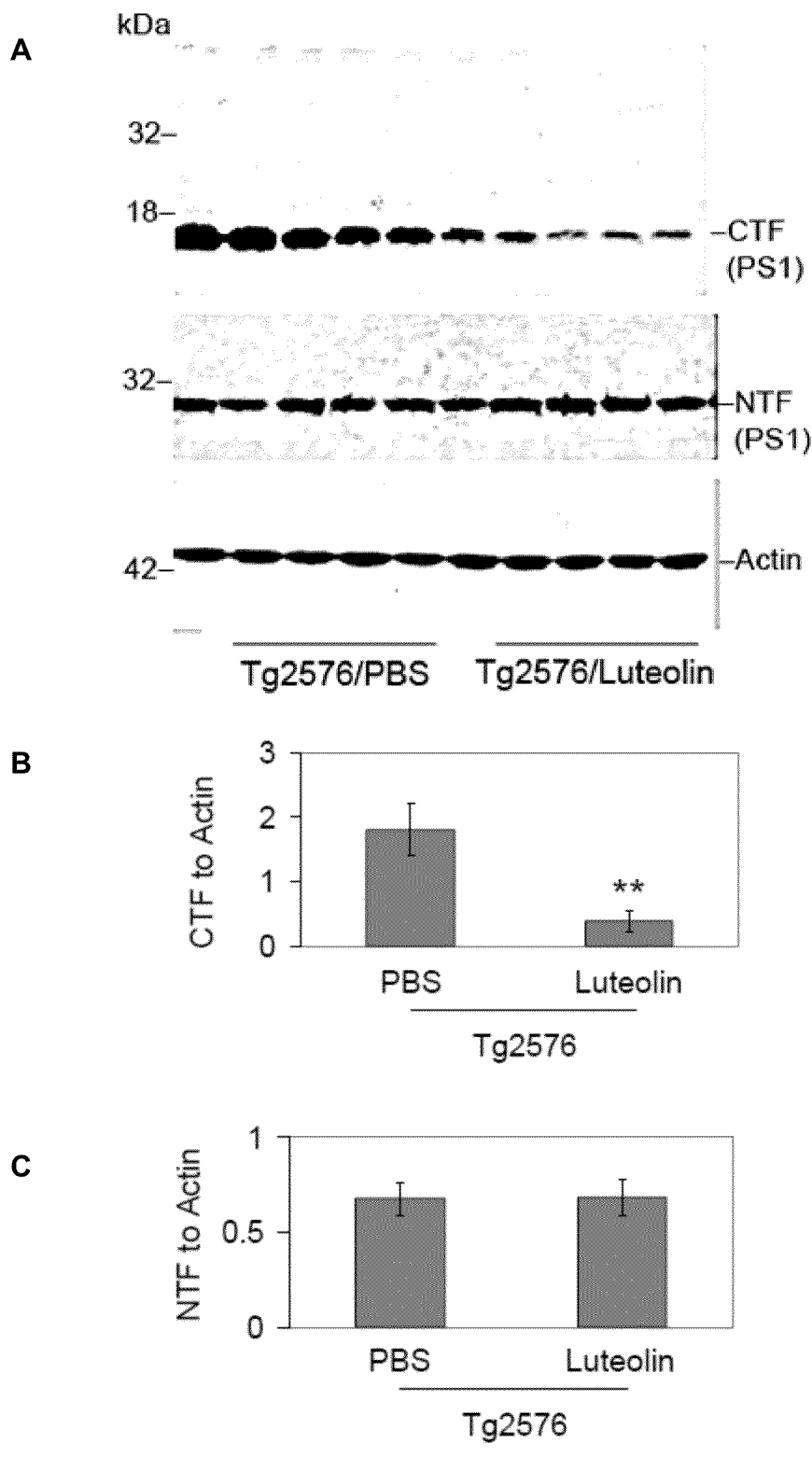
FIG. 29 show luteolin inhibits GSK-3 activation and cerebral amyloidosis in Tg2576 mice. Brain homogenates from Tg2576 mice treated with luteolin (n=5) or vehicle (PBS, n=5) and analyzed. (A) Western blot of brain homogenates were performed using anti-PS1 CTF or NTF antibody. Densitometric analysis produces the ratio of (B) PS1 CTF or (C) PS1 NTF to actin (internal control). A t test shows significant reductions in PS1 CTF levels with luteolin treatment (P<0.001), but not for PS1 NTF levels (P>0.05).
Figure 30:
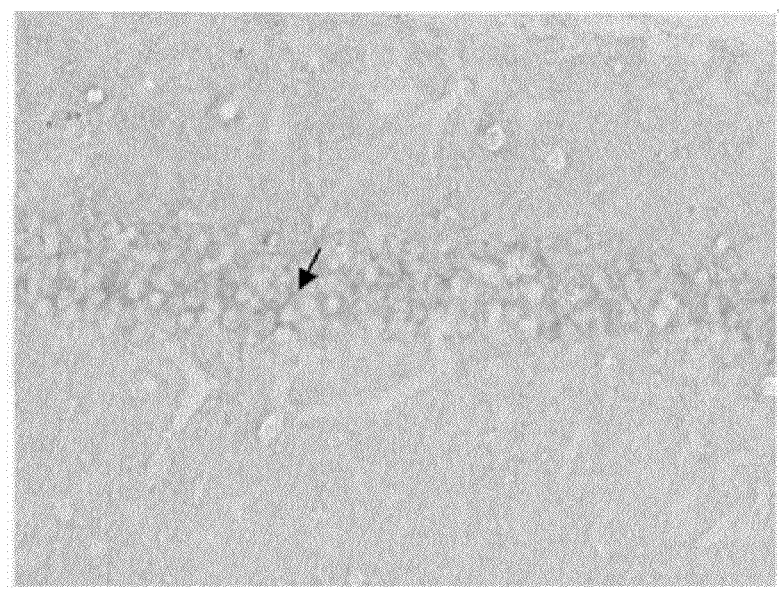
FIG. 30 is a cross sectional image of Tg2576 mouse brain after immunochemistry staining analysis. Tg2576 mice were treated with a PBS control or luteolin (20 mg/kg) for 30 days, before sacrifice. Brain sections were taken from indicated region and stained for phosphorylated GSK-3α/β.
Figure 31:
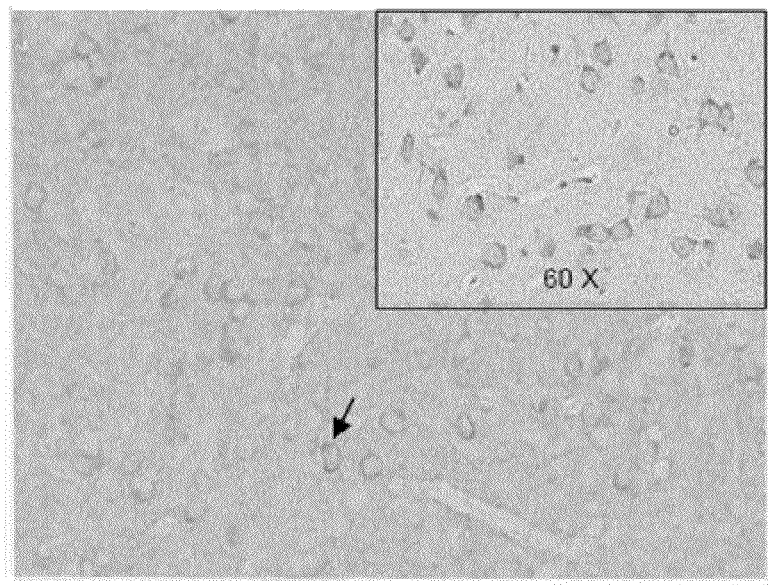
FIG. 31 is a cross sectional image of Tg2576 mouse brain after immunochemistry staining analysis. Tg2576 mice were treated with a PBS control or luteolin (20 mg/kg) for 30 days, before sacrifice. Brain sections were taken from indicated region and stained for phosphorylated GSK-3α/β.
Figure 32:
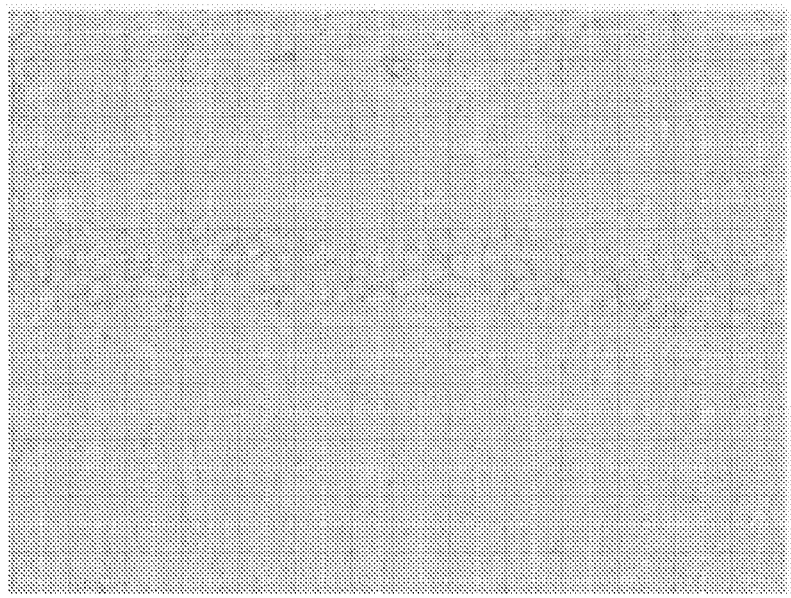
FIG. 32 is a cross sectional image of Tg2576 mouse brain after immunochemistry staining analysis. Tg2576 mice were treated with a PBS control or luteolin (20 mg/kg) for 30 days, before sacrifice. Brain sections were taken from indicated region and stained for phosphorylated GSK-3α/β.
Figure 33:
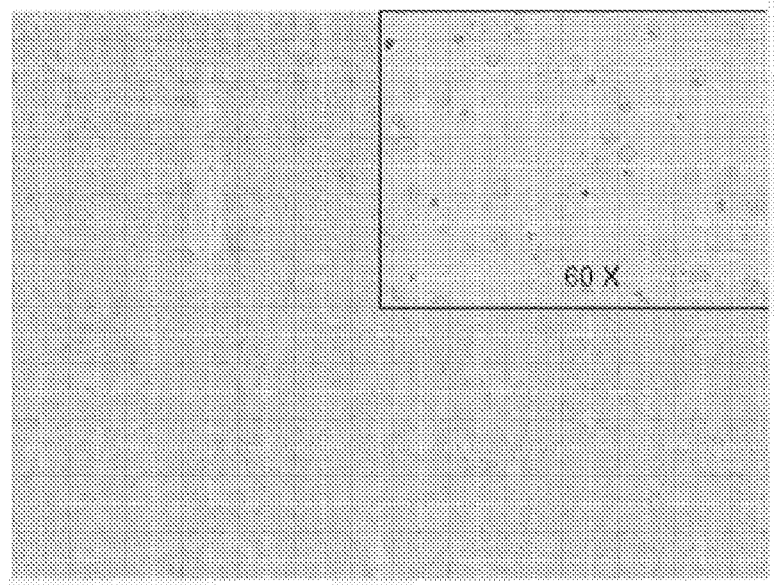
FIG. 33 is a cross sectional image of Tg2576 mouse brain after immunochemistry staining analysis. Tg2576 mice were treated with a PBS control or luteolin (20 mg/kg) for 30 days, before sacrifice. Brain sections were taken from indicated region and stained for phosphorylated GSK-3α/β.
Figure 34:
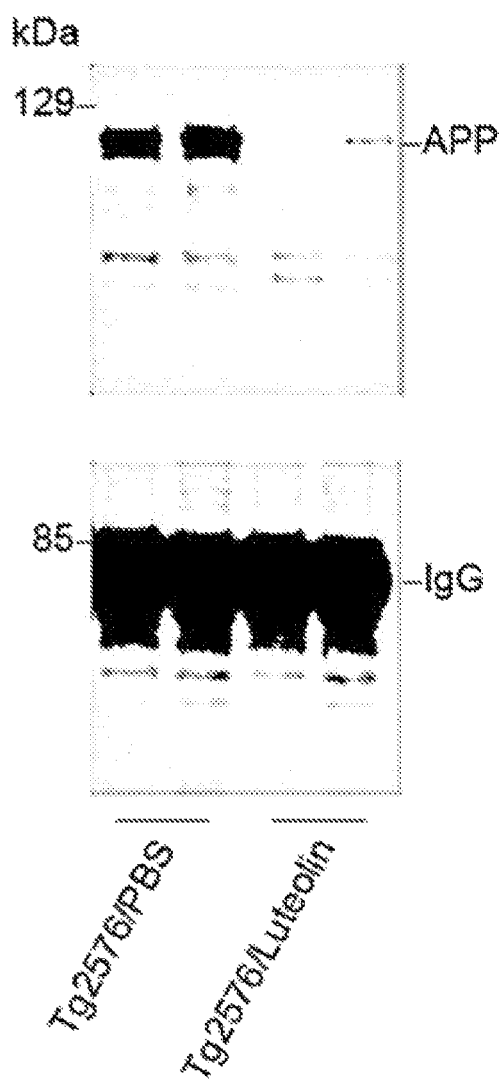
FIG. 34 is a blot depicting luteolin administration abrogates APP-PS1 interaction and indicating luteolin inhibits GSK-3 activation and cerebral amyloidosis in Tg2576 mice. Homogenates were immunoprecipitated by anti-PS1 CTF antibody and subjected to 6E10-probed Western blot. After administration of luteolin, APP signals disappear or drop sharply, indicating APP cannot adequately bind to PS1.

Brain homogenates from these mice were subsequently analyzed by immunoprecipitation, Western blot, and ELISA, seen in FIGS. 28(A) through 37. As shown in FIGS. 28(A) and 28(B), both GSK-3α/β active isoforms from the homogenates of luteolin treated mice are reduced when compared to control. Moreover, ratios of each phosphorylated GSK-3 isoform to its respective holo protein revealed a significant decrease in activation with treatment (P<0.001). See FIGS. 28(A) and 28(B). These decreases in activation also appeared in the immunohistochemical analysis of GSK-3α/β activity in neurons of the CA1 region of the hippocampus and regions of the cingulate cortex. See FIGS. 30 through 33. Western blot analysis of PS1 from treated mice shows significantly lower levels of PS1 processing, comparing CTF to actin ratios (P<0.001,). See FIGS. 29(A) and (C).

Figure 35:
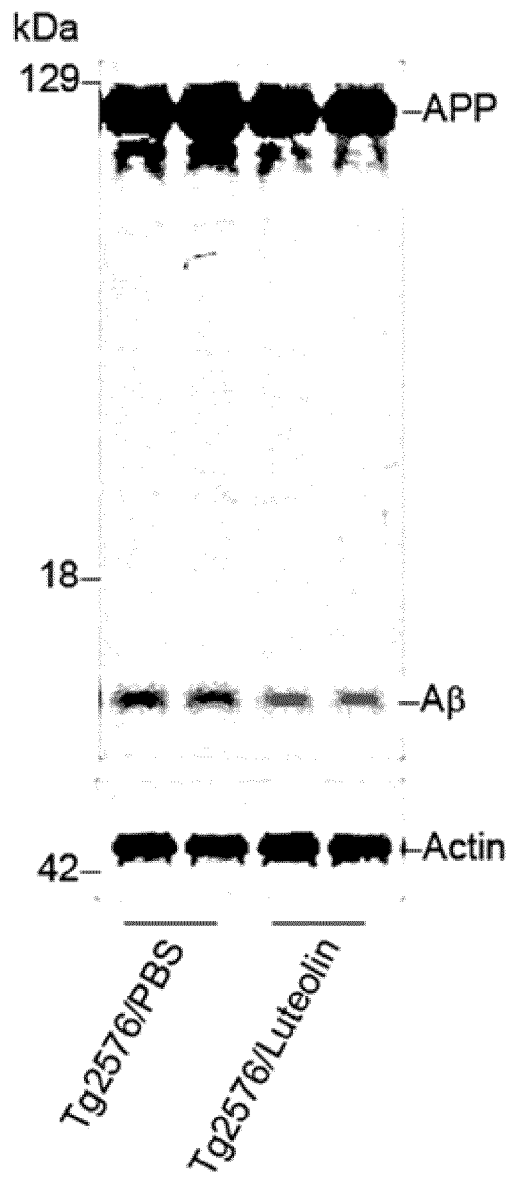
FIG. 35 is a blot showing luteolin administration does not impact APP precipitation. Homogenates were immunoprecipitated using 6E10 antibody and subjected to 6E10-probed Western blot. Administration of luteolin does not impact APP signals. Approximately 12 kD band may represent oligomeric form of amyloid.
Figure 36:
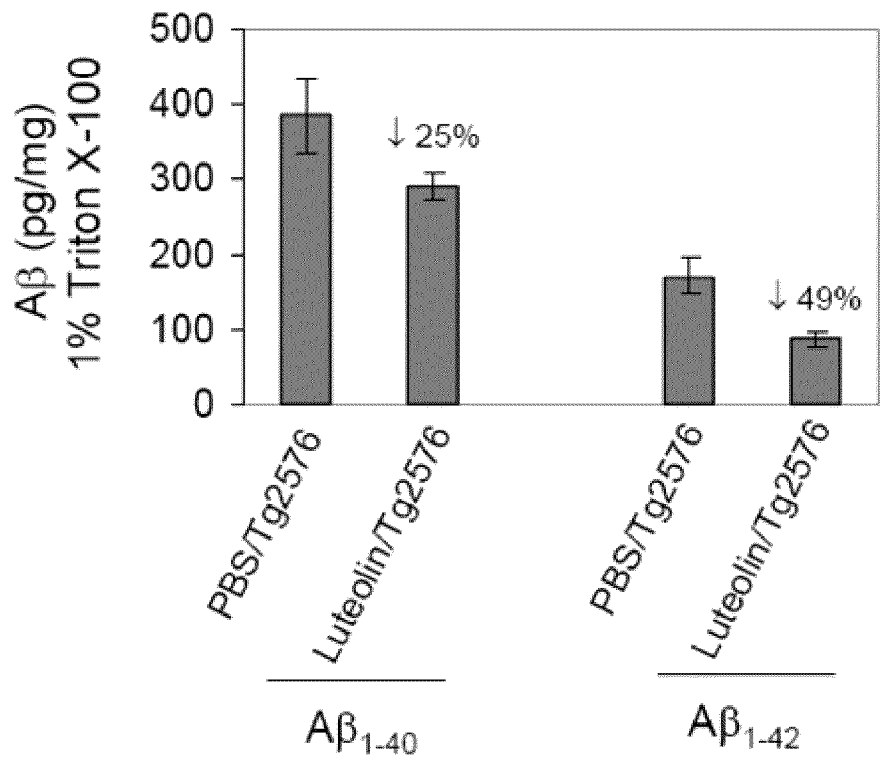
FIG. 36 is a graph of soluble and insoluble $A\beta_{1-40, 42}$ peptides from homogenates analyzed by ELISA. For Aβ ELISA, data are represented as picograms of peptide present in milligrams of total protein. Luteolin treatment results in markedly reduced soluble $A\beta_{1-40, 42}$ levels, 25% and 49%, respectively.
Figure 37:
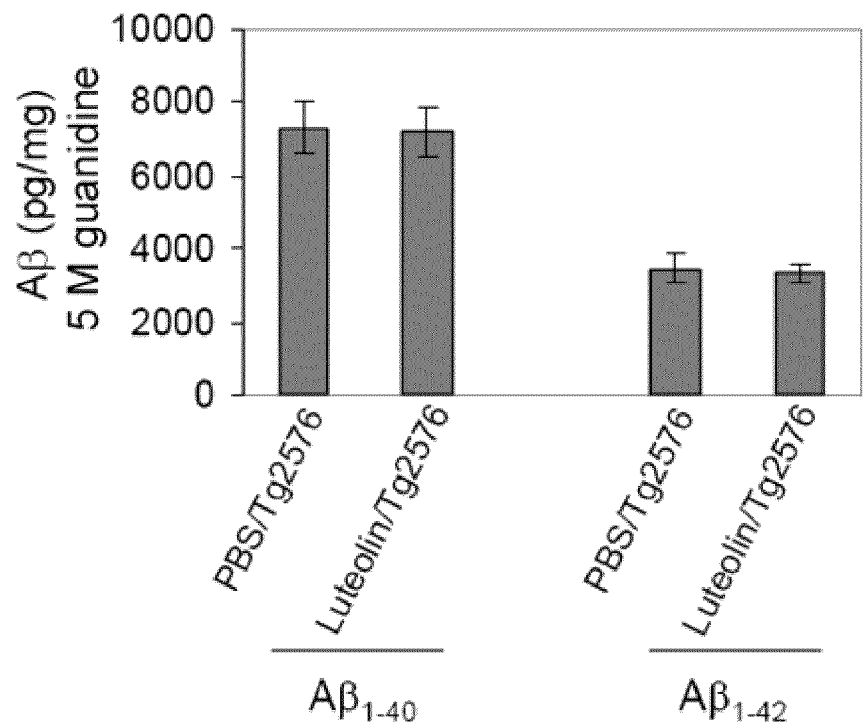
FIG. 37 is a graph of soluble and insoluble $A\beta_{1-40, 42}$ peptides from homogenates analyzed by ELISA. For Aβ ELISA, data are represented as picograms of peptide present in milligrams of total protein. No significant reductions in insoluble Aβ isoforms following treatment were observed.

Brain homogenates were immunoprecipitated by PS1 antibody and probed for APP to confirm the proposed mechanism. Luteolin treatment effectively abolished PS1-APP association, seen in FIG. 34. Also, no significant changes in holo APP expression were observed following treatment and a potential decrease in oligomeric forms of Aβ even detected as illustrated in FIG. 35. To assess this decrease, ELISA was conducted on both soluble and insoluble Aβ$_{1-40, 42}$. See FIGS. 34 and 35. Luteolin treatment markedly reduced soluble isoforms of Aβ$_{1-40, 42}$ by 25% and 49%, respectively, depicted in FIG. 34, but no such reductions in insoluble Aβ isoforms were identified, seen in FIGS. 36 and 37.

EXAMPLE 4

Oral Administration of Diosmin Reduces AP Pathology in Tg2576 Mice

Eight month-old Tg2576 mice were treated with a 0.05% diosmin (>90% purity by HPLC), purchased from Axxora (San Diego, Calif.) diet (in standard mouse chow) for 6 months to validate the above findings in vivo. Mice were anethetized with isofluorane and transcardinally perfused with ice-cold physiological saline containing heparin (10 U/mL). Brains were rapidly isolated and quartered using a mouse brain slicer. The first and second anterior quarters were homogenized for Western blot analysis, and the third and fourth posterior quarters were used for microtome or cryostat sectioning. Brains were then fixed in 4% paraformaldehyde in PBS at 4° C. overnight and routinely processed in paraffin in a core facility at the Department of Pathology (USF College of Medicine). Five coronal sections from each brain (5-μm thickness) were cut with a 150-μm interval. Sections were routinely deparaffinized and hydrated in a graded series of ethanol baths prior to pre-blocking for 30 min at ambient temperature with serum-free protein block. Aβ immunohistochemical staining was performed using anti-human amyloid-β antibody (4G8) in conjunction with the VectaStain Elite ABC kit coupled with diaminobenzidine substrate. β-amyloid plaques positive for 4G8 were visualized under bright field using an Olympus BX-51 microscope. Aβ burden was determined by quantitative image analysis. Briefly, images of five 5-μm sections (150 μm apart) through each anatomic region of interest (hippocampus and neocortex) were captured and a threshold optical density was obtained that discriminated staining from background. Manual editing of each field was used to eliminate artifacts. Data are reported as percentage of immunolabeled area captured (positive pixels divided by total pixels captured). Quantitative image analysis was performed by a single examiner (TM) blinded to sample identities.

Figure 38:
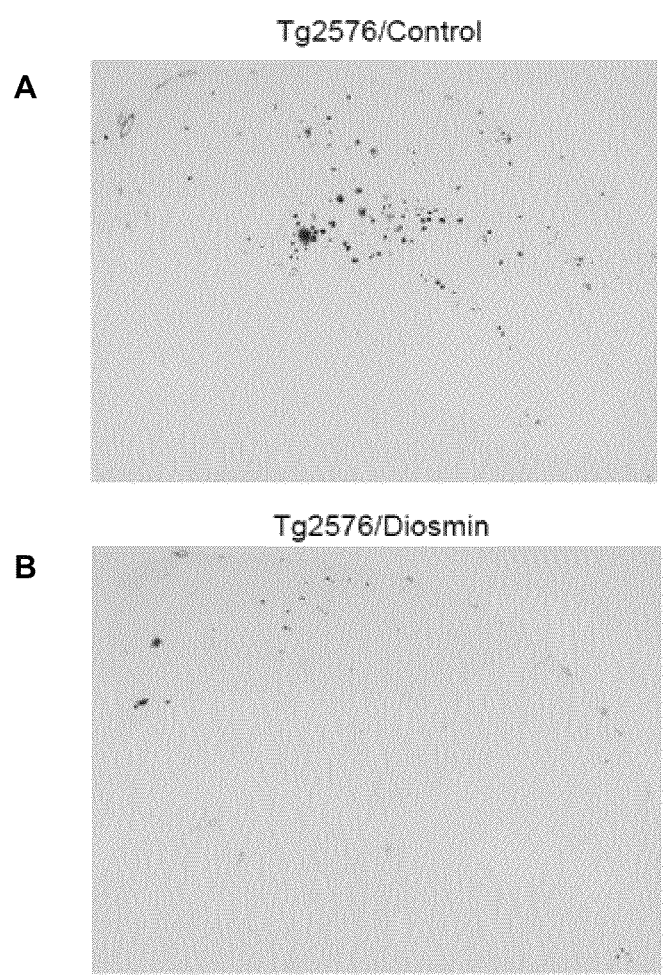
FIG. 38 is a cross sectional image of Tg2576 mouse brain after immunochemistry staining analysis. Tg2576 mice were treated with control or 0.05% diosmin diet for 6 months, before sacrifice. Brain sections stained for Aβ plaques with 4G8 antibody.

Pharmacokinetic studies suggest luteolin has an oral bioavailability <2% and a half-life in plasma <4 hrs. Therefore, other compounds with a 5,7-dihydroxyflavone structural backbone were screened to identify a more suitable flavonoid for oral administration. One flavonoid compound, diosmetin, proved to be just as efficacious as luteolin in promoting PS1 CTF phosphorylation and consequently inhibiting γ-secretase activity in SweAPP N2a cells (data not shown). Diosmin, a well-evidenced vascular protecting agent, is rapidly transformed by intestinal flora to its aglycone form, diosmetin. Taken in this manner, diosmetin was found to be readily absorbed and rapidly distributed throughout the body with a plasma half-life >26 hrs. To determine whether oral administration of diosmin, as a parent compound for diosmetin, could have similar anti-amyloidogenic effects in vivo as luteolin, Tg2576 mice were orally treated with 0.05% diosmin supplemented or control diet at 8 months of age for 6 months. As shown in FIGS. 38(*a*) to 40, diosmin treatment similarly reduced Aβ deposition in these mice. Image analysis of micrographs from Aβ antibody (4G8) stained sections reveals that plaque burdens were significantly reduced throughout the brain (P<0.001). See FIGS. 38(*a*) and (*b*). Amyloid plaque burden was assessed by quantifying 4G8 positive stained plaques using image analysis, seen in FIG. 39. To verify the findings from these coronal sections, brain homogenates were analyzed for Aβ levels by ELISA. Diosmin oral treatment markedly decreased both soluble and insoluble forms of $Aβ_{1-40, 42}$. Diosmin treatment results in markedly reduced total soluble and insoluble $Aβ_{1-40, 42}$ levels, to 37% and 46%, respectively. See FIG. 40. Taken together, the above data confirm an oral route of administration of diosmin provides effective, if not superior, attenuation of amyloid pathology comparable to that of i.p injected luteolin.

GSK-3α inhibition has been shown to promote the phosphorylation of the CTF of PS1, whether achieved by pharmacological means or by genetic silencing. This phosphorylation subsequently disrupts the enzyme-substrate association with APP. During in vitro validation, significant increases in PS1 CTF phosphorylation (20 kD isoforms) were observed during luteolin, SB-415286, and GSK-3α RNAi treatment, which act with similar potency (luteolin and SB-415286) and efficacy. See FIGS. 24(A) through 25(B). Both in vitro and in vivo analysis reveal significant reductions in APP co-immunoprecipitated with PS1 following treatment, as seen in FIGS. 26(A) through 27(B) and 34 through 33. Further, γ-secretase activity decreases in a dose- and time-dependent manner, seen in FIGS. 9(*a*) through 10(*b*), GSK-3α inhibition does not appear to phosphorylate full-length PS1 and does not affect endoproteolytic cleavage based on PS1 NTF analysis, as seen in FIGS. 23(A) and (B). Although phospho-PS1 CTFs were not detected in vivo, reductions in the 16 kD PS1 CTF bands, seen in FIGS. 29(A) through (C), were detected, which are indicative of a more highly active, amyloidogenic γ-secretase complex. Therefore, these compounds affect γ-secretase at the level of the CTF of PS1. There are some obvious complexities to the mechanism of dimerization of PS1 along with subsequent association with other essential γ-secretase components such as nicastrin, which recent studies suggest may function as the γ-secretase substrate receptor.

EXAMPLE 5

Screening of Flavonoid Compounds for Reduction of Aβ Pathology

Figure 41:
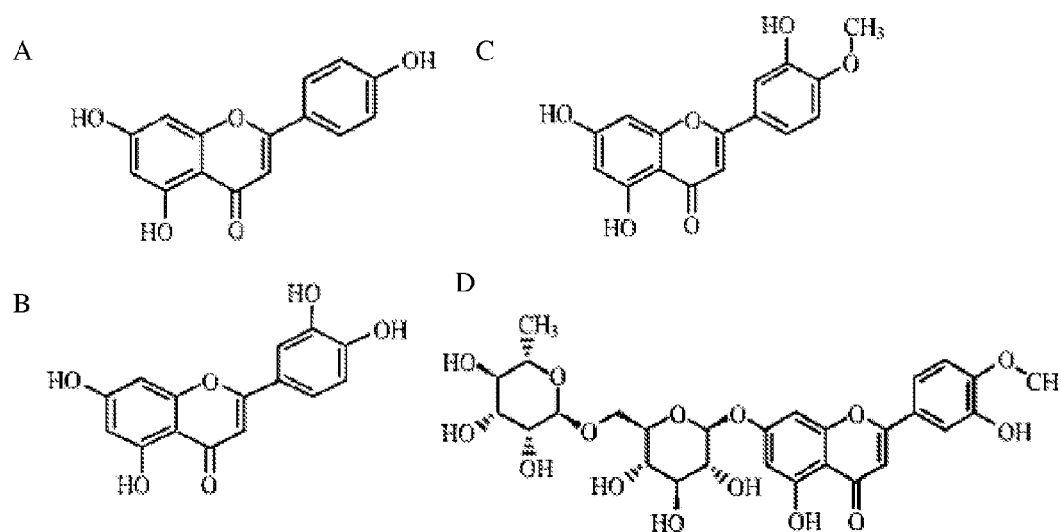
FIG. 41(a)-(d) are compound structures of (a) apigenin, (b) luteolin, (c) diosmetin, and (d) diosmin.
Figure 42:
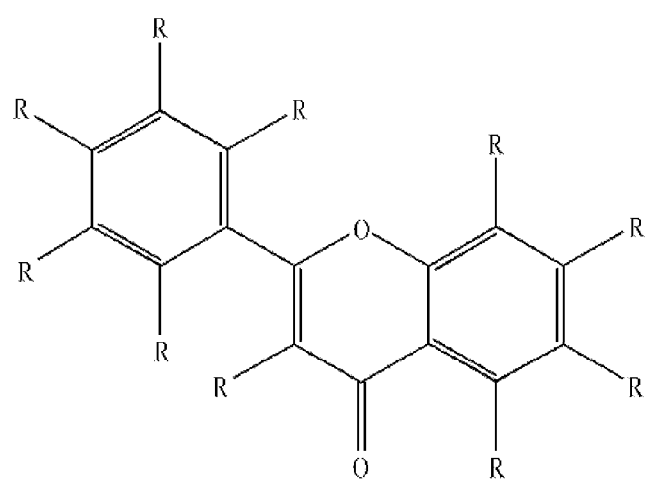
FIG. 42 is the functional backbone structure of the present invention.
Figure 43:
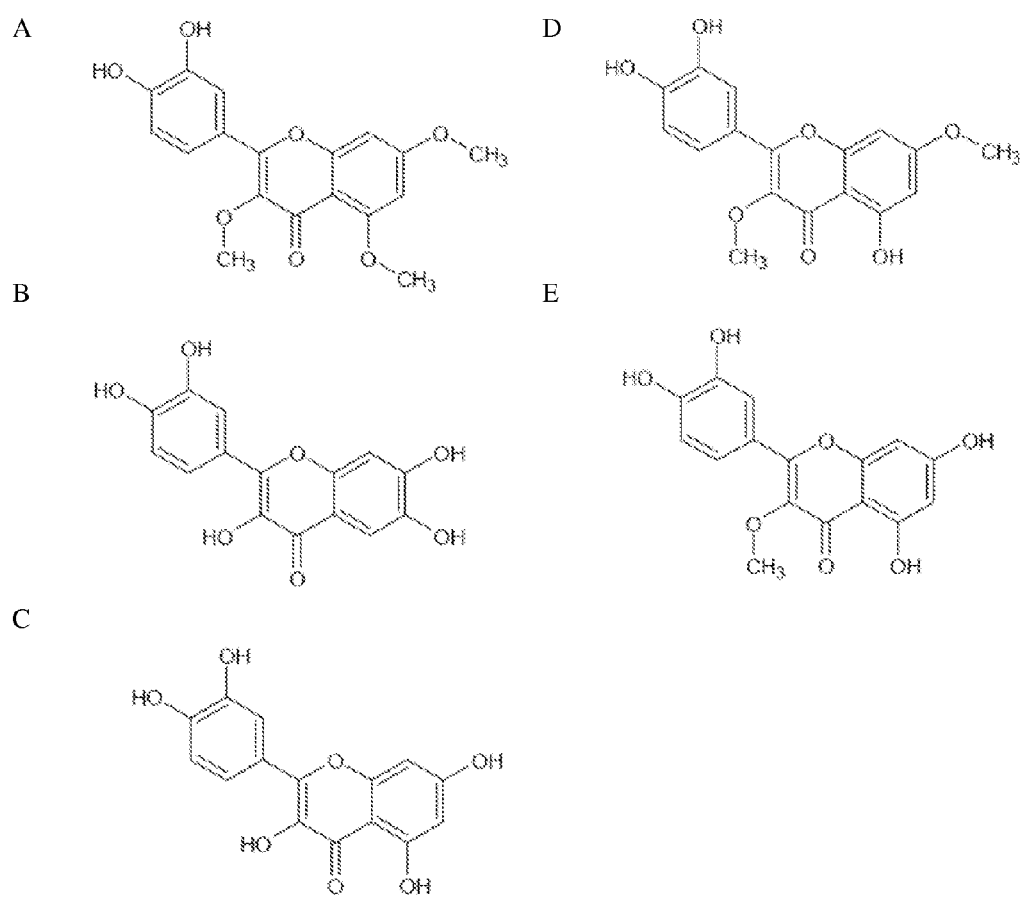
FIG. 43(a)-(e) are compound structures of (a) CID 147651, 2-(3,4-dihydroxyphenyl)-3,5,7-trimethoxychromen-4-one.
Figure 44:
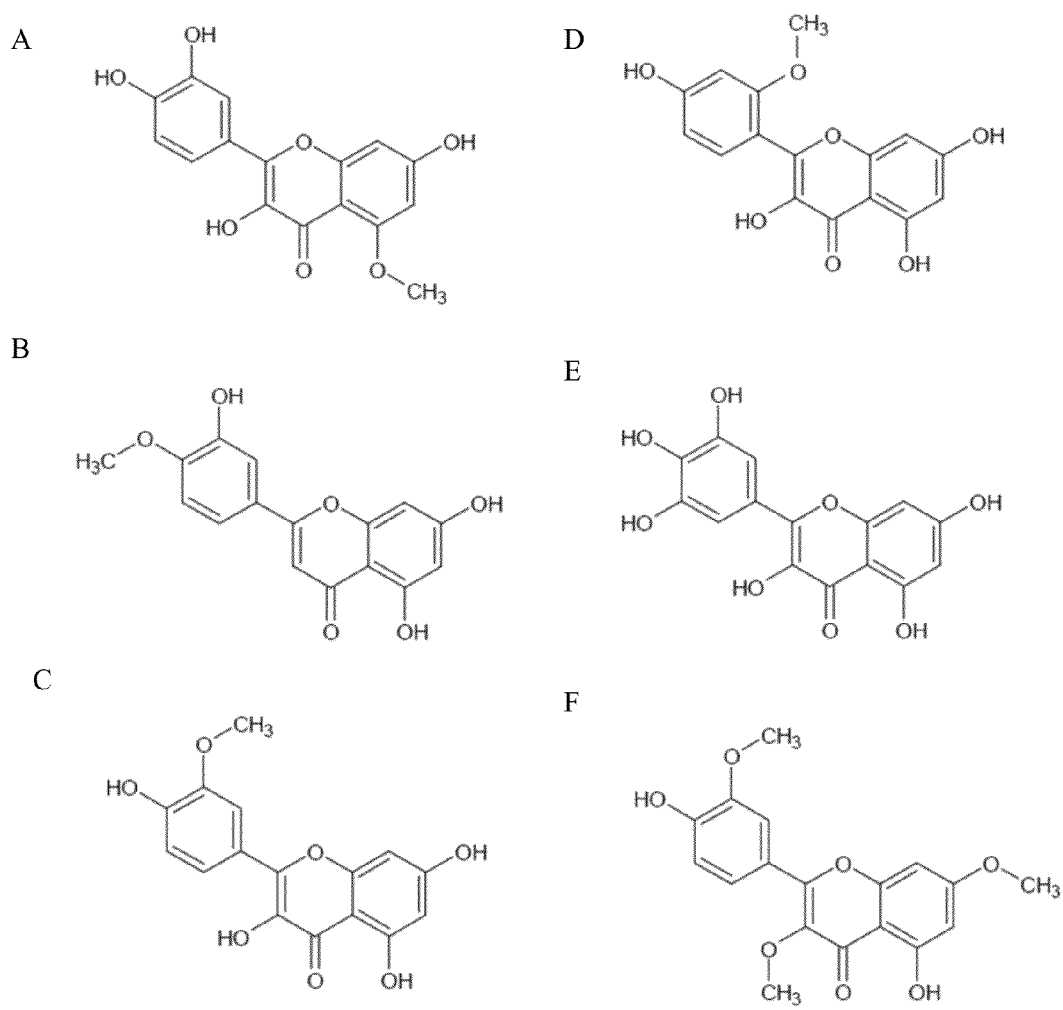
Figure 45:
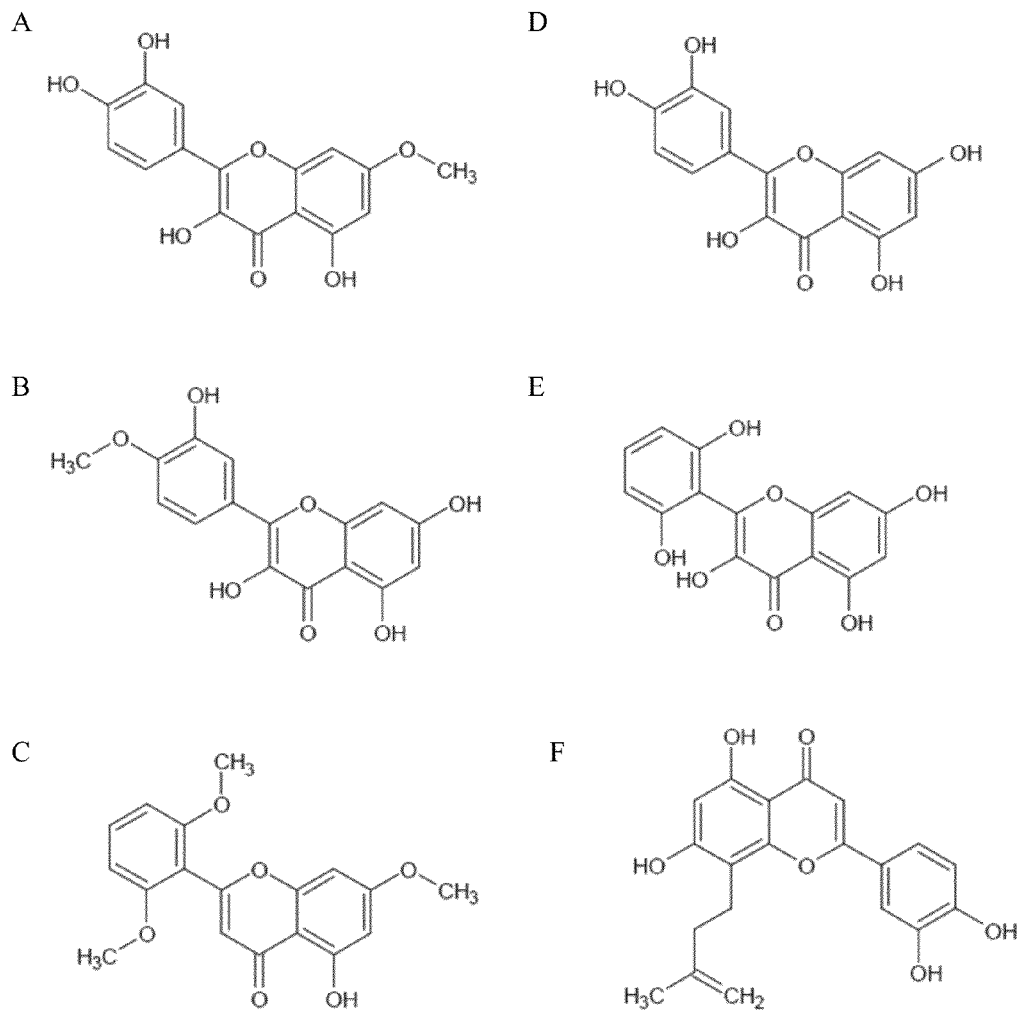
Figure 46:
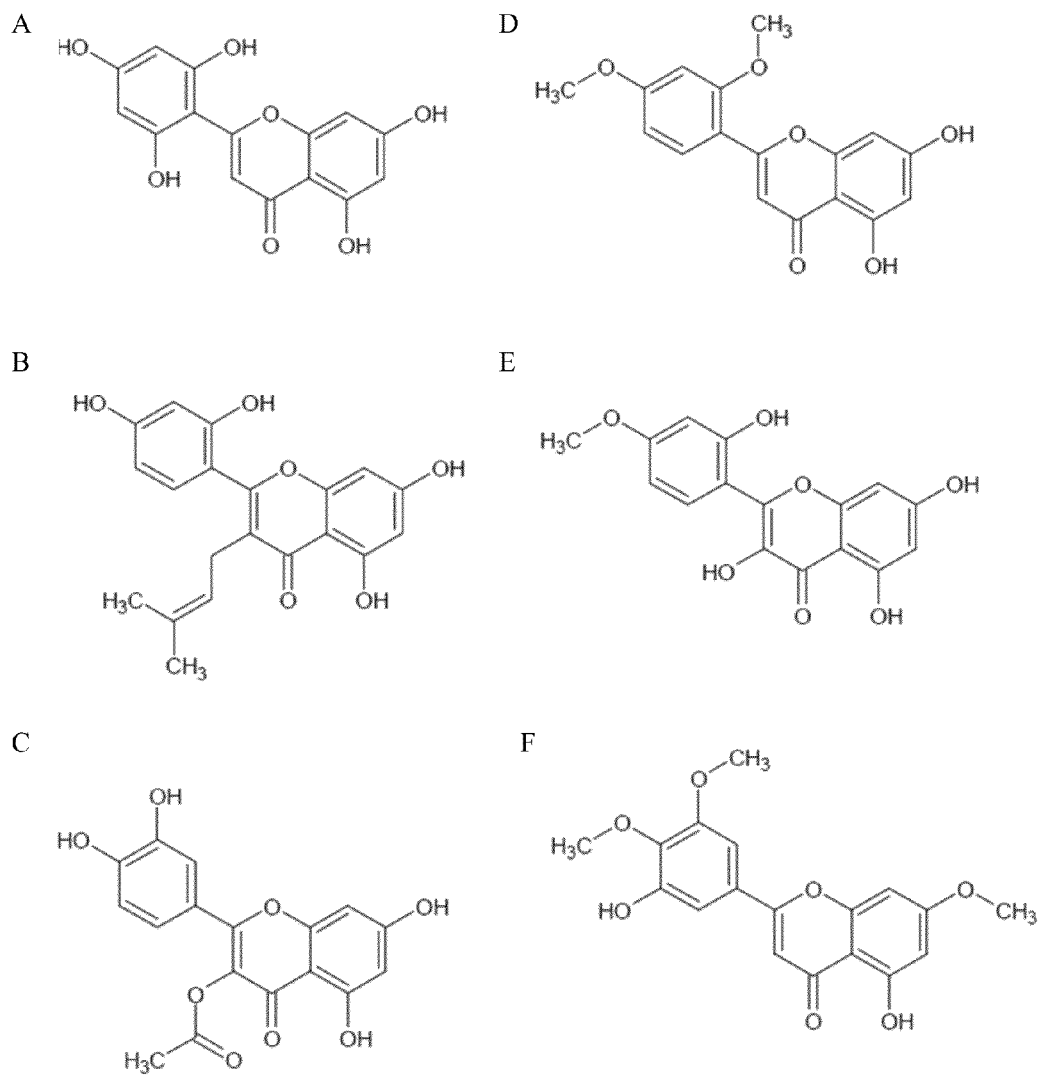
Figure 47:
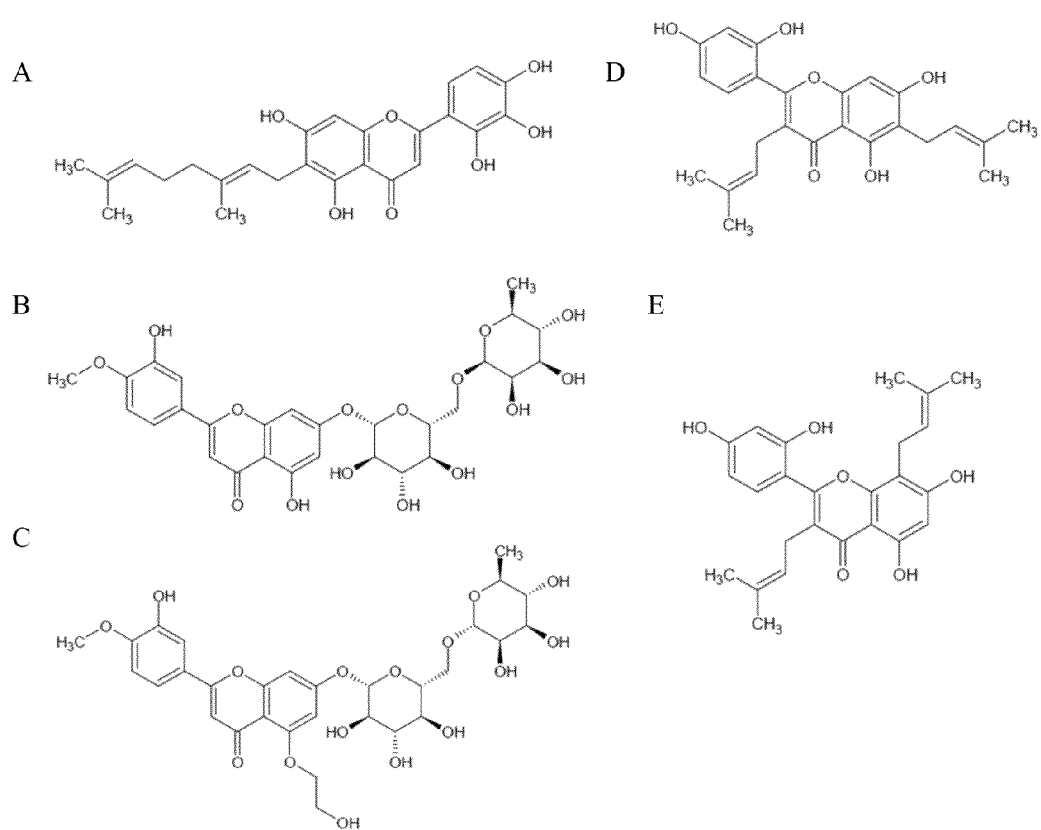
Figure 48:
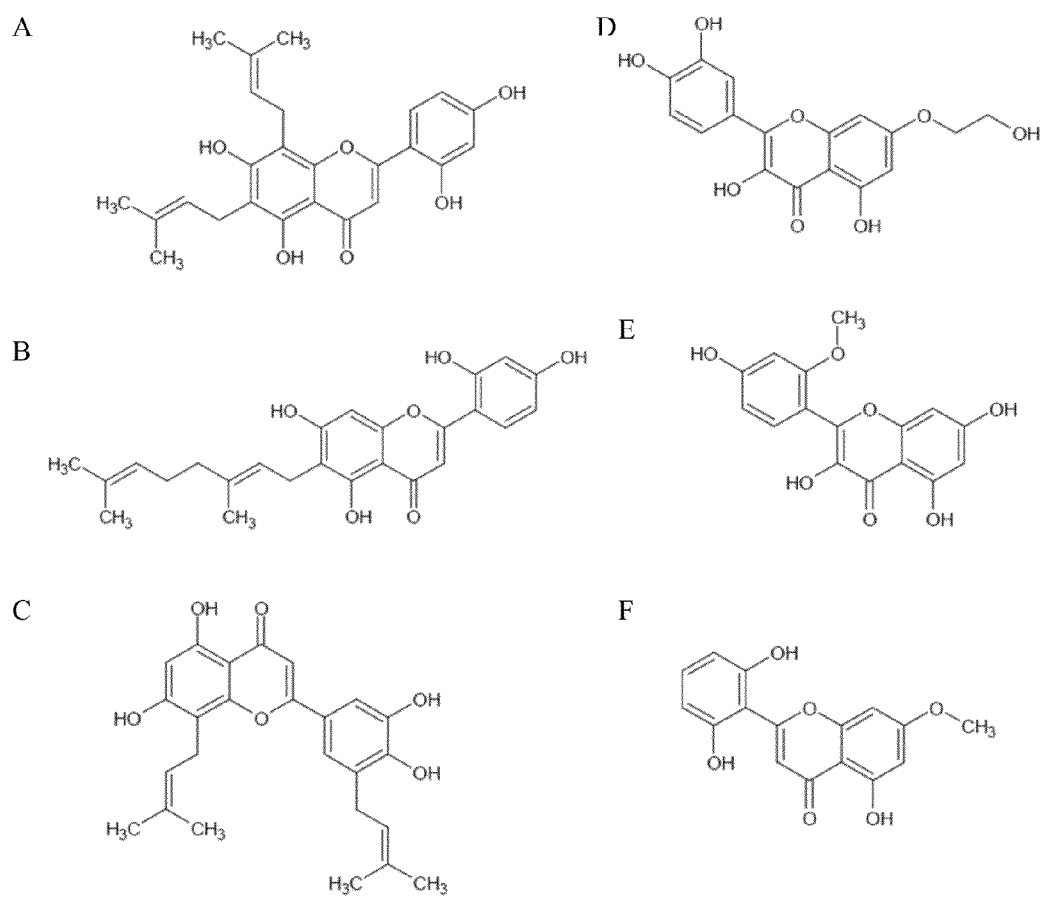

Various flavonoids, specifically flavones, were screened for an effect on APP proteolysis using immunoprecipitation (IP), Western blot, and ELISA on cellular extracts. FIG. 41 shows a list of flavones that were screened for an effect γ-secretase and $Aβ_{1-40, 42}$ production in either cell line in a dose dependent manner. Apigenin, seen in FIG. 41(*a*), did not reduce $Aβ_{1-40, 42}$ production to the same level as luteolin, diosmetin, and diosmin, seen in FIGS. 41(*b*)-(*d*), respectively. An analysis of the structure showed that the structural backbone, seen in FIG. 42, of the compound is responsible for the exhibited activity. Oxygen moieties, including hydroxy, methoxy, carbonyl and oxyalkyl, oxyaryl, and oxyalkenes, are required on both rings of the backbone structure. Compounds useful in the present invention include exemplary compounds seen in FIGS. 43(*a*)-54.

The presence of phosphorylated PS1 CTFs corresponds with reduction of Aβ generation and accumulation of the β-CTF of APP, as was observed following luteolin treatment. See FIGS. 1 through 10(B). The accumulation β-CTFs following luteolin treatment is a fraction of β-CTF seen after direct γ-secretase inhibitor treatment (data not shown). In view of this finding, selective GSK-3 inactivation is a less toxic, more regulative, substrate-specific mode of γ-secretase inhibition. Earlier studies routinely employed phorbol-12,13-dibutyrate (PDBu), a potent PKC activator, as their phosphorylating agent. Thus, luteolin was tested for similar PKC activation, rather than a GSK-3 inhibitor. Co-treatment of SweAPP N2a cells with luteolin or SB-415286 and the PKC inhibitor GF109203X had no effect on GSK-3 inhibition (data not shown). Minor decreases in 20 kD and 18 kD phospho-PS1 CTF isoforms following GF109203X treatment, indicate PKC may play a part either in the downstream signaling mechanism or by directly phosphorylating the PS1 CTF. Additionally, there are no indications GSK-3α inhibition affects non-amyloidogenic processing of APP, since luteolin, SB-415286, and GSK-3α RNAi treatment have no effect on the maturation of TACE, ADAM10, or sAPPα release (data not shown), which are all strongly associated with PKC activation. This data indicates GSK-3α is an upstream regulator of PS1 CTF phosphorylation and consequently of γ-secretase activity.

Figure 13:
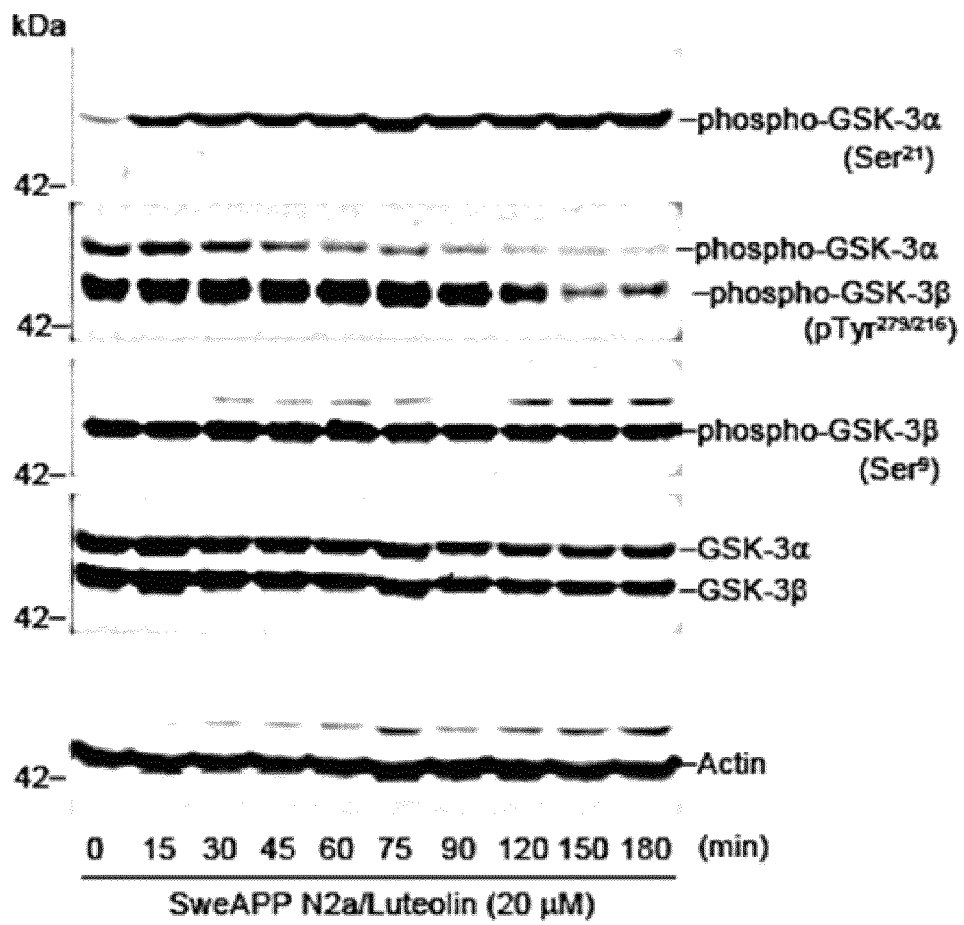
FIG. 13 is a blot showing luteolin selectively inactivates GSK-3α. SweAPP N2a cells were treated with luteolin at 20 μM for various time points as indicated. Cell lysates were prepared and subjected to Western blot analysis in phosphorylated forms of GSK-3α/β. Western blot analysis using anti-phospho-GSK-3α/β(Tye$^{279/216}$) antibody shows two bands (51 and 47 kDa) corresponding to phosphorylated forms of GSK-3α and GSK-3β or using anti-phospho-GSK-3β (Ser$^9$) antibody recognizes phosphorylated form of GSK-3β at 47 kDa. Anti-actin antibody was used as shows an internal reference control. Densitometry analysis shows the ratio of phospho-GSK-3α (Tye$^{279/216}$) to total GSK-3α as indicated below the figures (n=3 for each condition). A significant difference was noted between 30 min and 45, 60, 75, 90, 120, 150 or 180 min (P<0.005).
Figure 14:
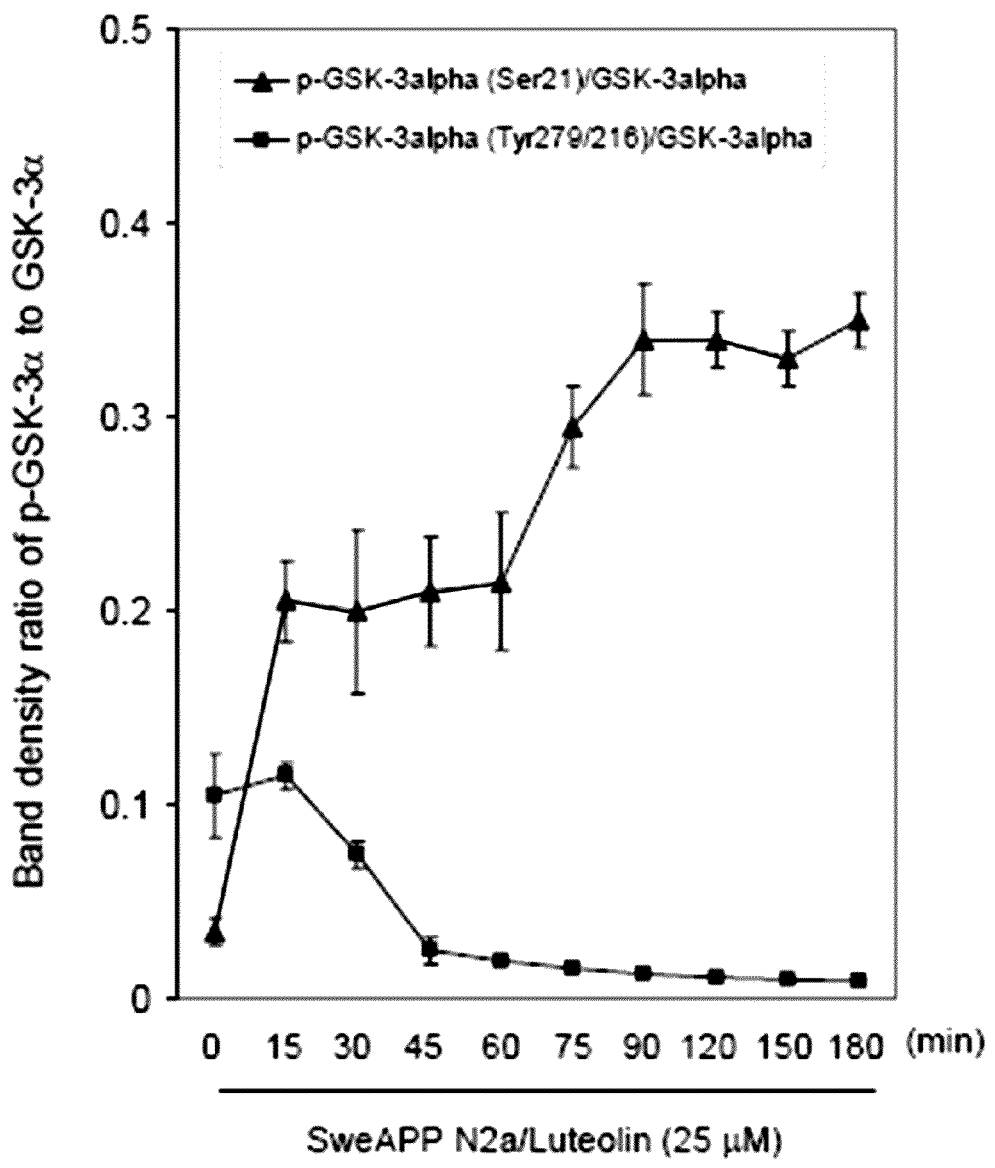
FIG. 14 is a graph showing luteolin selectively phosphorylates Serine 21 of GSK-3α. SweAPP N2a cells were treated with 20 μM luteolin for various time points as indicated. Cell lysates were prepared and subjected to Western blot analysis. Anti-phospho-GSK-3α (Ser$^{21}$) antibody shows one band (51 kDa) corresponding to phosphorylated form of GSK-3α or using anti-GSK-3 monoclonal antibody recognizes both total GSK-3α and GSK-3β, 51 and 47 kDa, respectively. Western blot analysis using anti-actin antibody shows actin protein (as an internal reference control). Densitometry analysis shows the ratio of phospho-GSK-3α (Ser$^{21}$) to total GSK-3α as indicated below the figures (n=3 for each condition). One-way ANOVA followed by post hoc comparison revealed a significant difference between 0 min and 5, 10, 15, 20 or 25 min (P<0.001).
Figure 15:
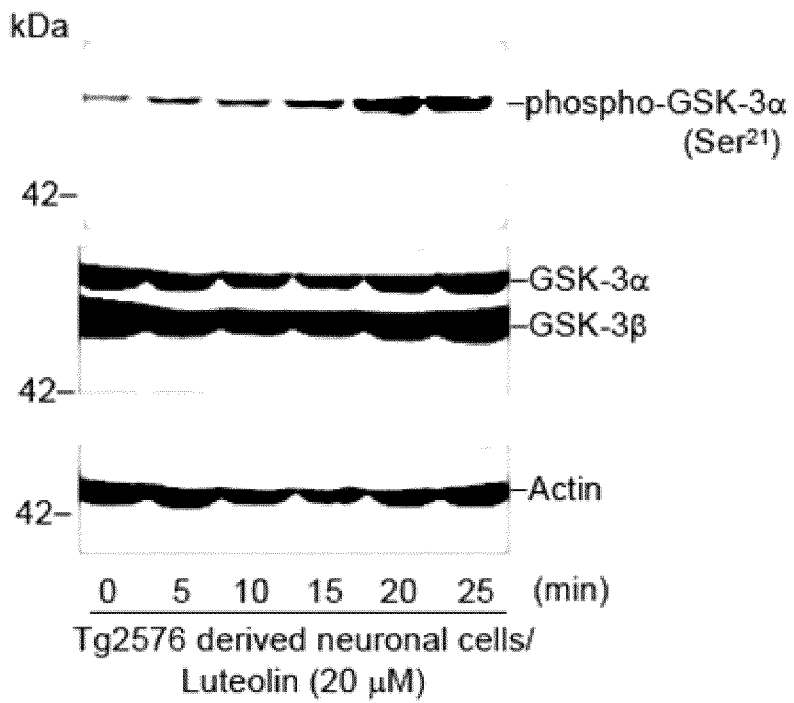
FIG. 15 is a blot showing luteolin selectively phosphorylates Serine 21 of GSK-3α. Tg2576 derived neuronal cells were treated with 20 μM luteolin for various time points as indicated. Cell lysates were prepared and subjected to Western blot analysis in phosphorylated forms of GSK-3α/β. Western blot analysis using anti-phospho-GSK-3α/β (Tye$^{279/216}$) antibody shows two bands (51 and 47 kDa) corresponding to phosphorylated forms of GSK-3α and GSK-3β or using anti-phospho-GSK-3β (Ser$^9$) antibody recognizes phosphorylated form of GSK-3β at 47 kDa. Anti-actin antibody was used as shows an internal reference control.
Figure 16:
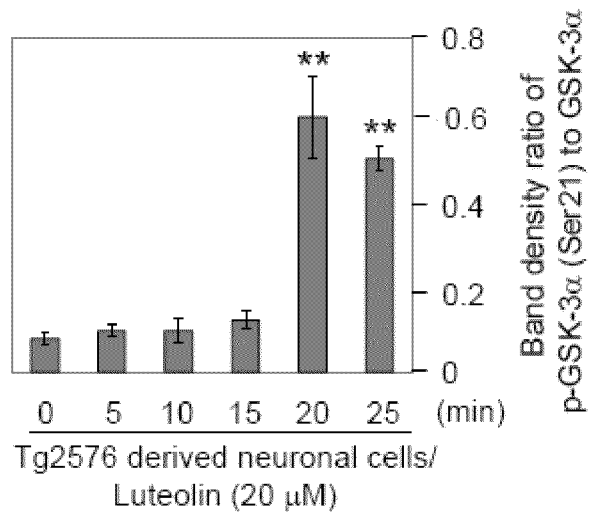
FIG. 16 is a graph of the blot in FIG. 15, and showing luteolin selectively phosphorylates Serine 21 of GSK-3α. Densitometry analysis shows the ratio of phospho-GSK-3α (Tye$^{279/216}$) to total GSK-3α as indicated below the figures (n=3 for each condition). A significant difference was noted between 30 min and 45, 60, 75, 90, 120, 150 or 180 min (P<0.005).
Figure 17:
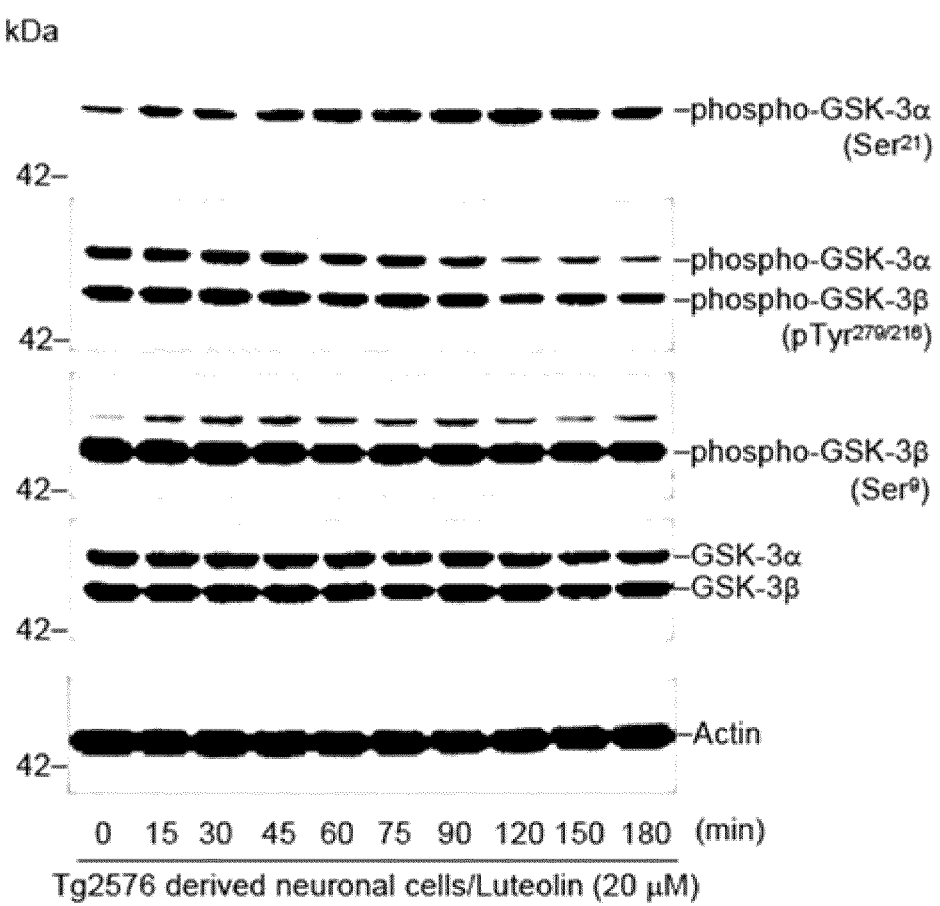
FIG. 17 is a blot indicating luteolin selectively inactivates GSK-3α. Tg2576 derived neuronal cells were treated with luteolin at 20 μM for various time points as indicated. Cell lysates were prepared and subjected to Western blot analysis in phosphorylated forms of GSK-3α/β. Western blot analysis using anti-phospho-GSK-3α (Ser$^{21}$) antibody shows one band (51 kDa) corresponding to phosphorylated form of GSK-3α or using anti-GSK-3 monoclonal antibody recognizes both total GSK-3α and GSK-3β, 51 and 47 kDa, respectively. Anti-phospho-GSK-3α/β(Tye$^{279/216}$) antibody shows two bands (51 and 47 kDa) corresponding to phosphorylated forms of GSK-3α and GSK-3β or using anti-phospho-GSK-3α/β (Ser$^9$) antibody recognizes phosphorylated form of GSK-3β at 47 kDa. Anti-actin antibody was used as an internal reference control.
Figure 18:
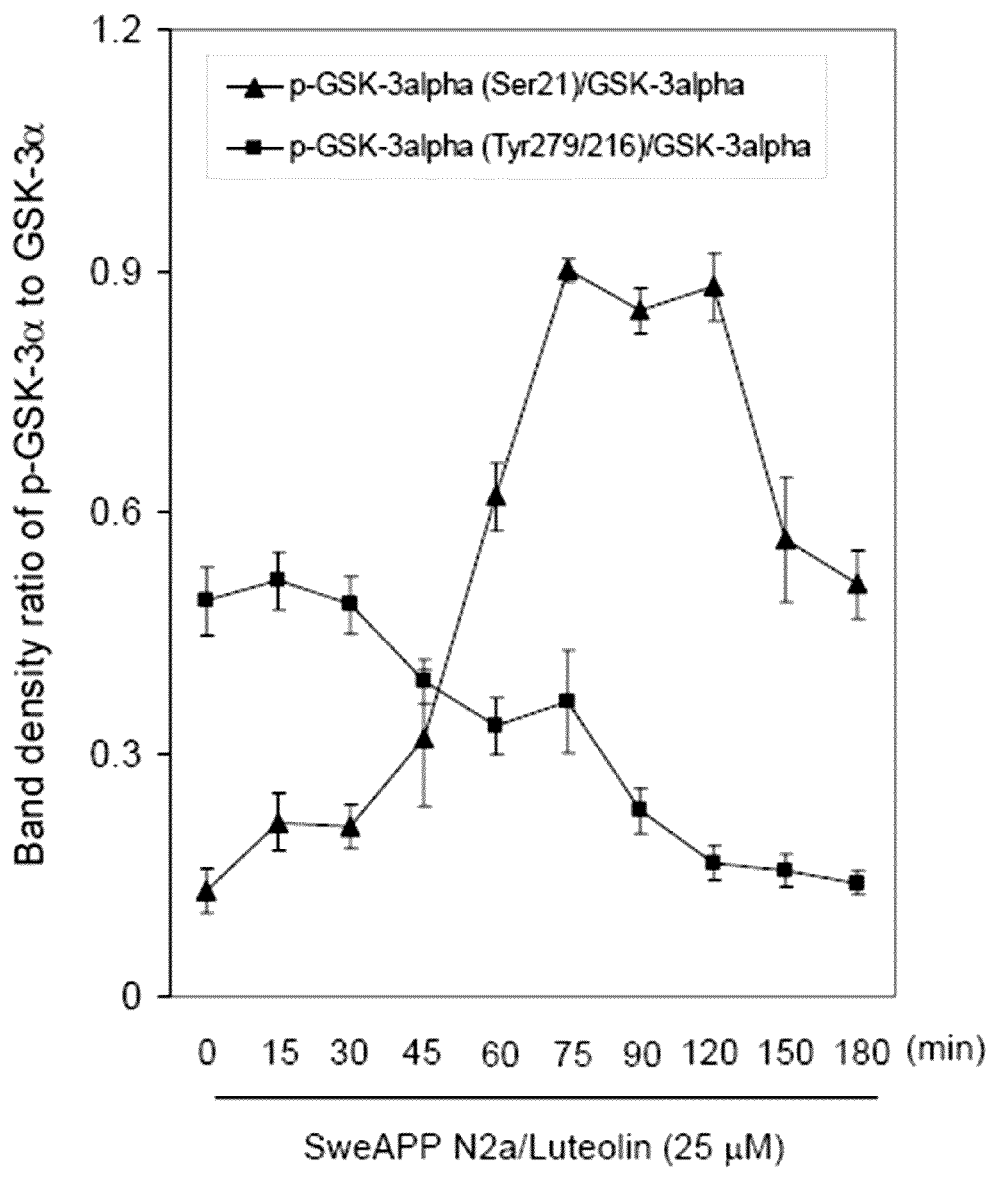
FIG. 18 is a graph of the protein levels of GSK-3α and GSK-3β following luteolin treatment. SweApp N2a cells were treated with 25 μM luteolin for the times indicated. Cell lystaes were prepared and subjected to Western blot, probing for anti-phospho-GSK-3α (Ser$^{21}$) and phospho-GSK-3α (Tye$^{279/216}$). Densitometry analysis was conducted of the ratio of phospho-GSK-3α (Ser$^{21}$) to total GSK-3α or phospho-GSK-3α (Tye$^{279/216}$) to total GSK-3α (n=3 for each condition). One-way ANOVA followed by post hoc comparison revealed a significant difference between 30 min and 45, 60, 75, 90, 120, 150 or 180 min (P<0.005).
Figure 19:
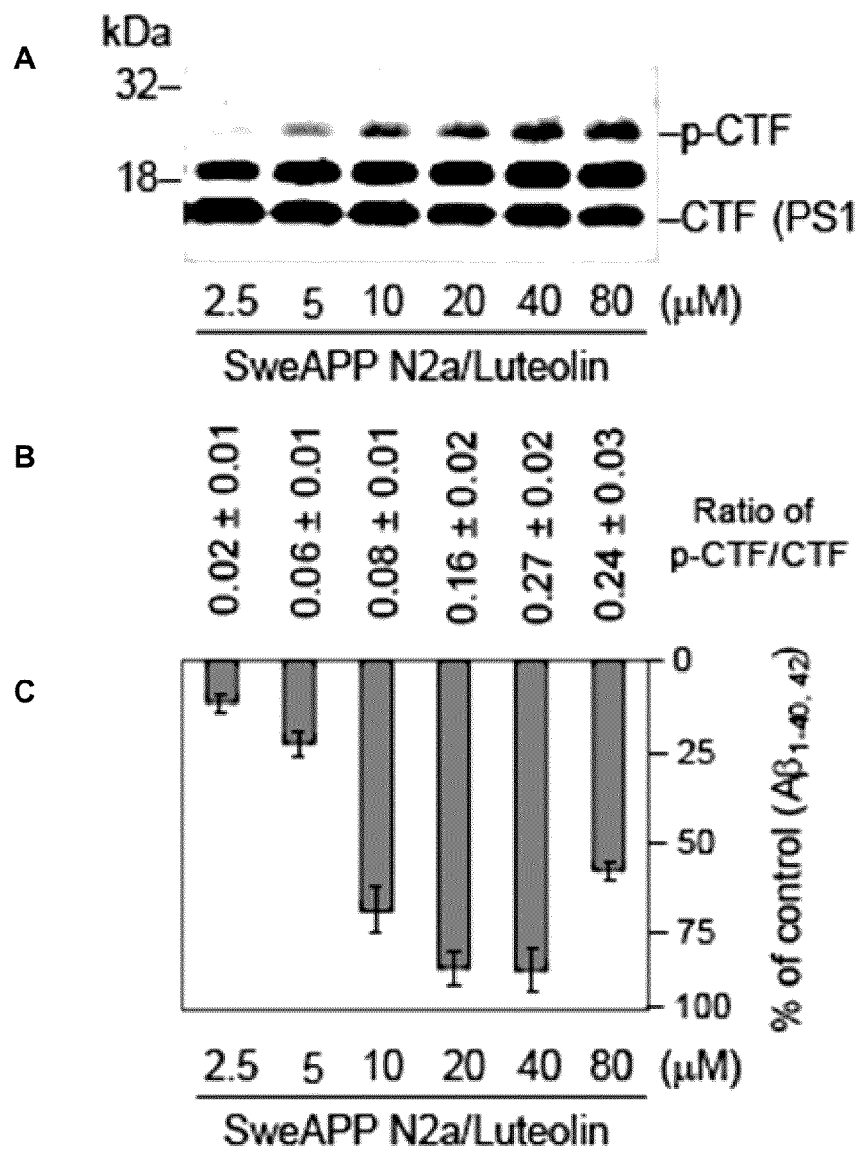
FIG. 19 is a blot showing PS1 phosphorylation is associated with luteolin-mediated inhibition of Aβ generation. SweAPP N2a cells were treated with luteolin at indicated doses for 4 hrs. Cell lysates were prepared from these cells and subjected to Western blot analyses of PS1 C-terminal fragments (CTF). (A) Western blot analysis by anti-PS1 CTF antibody shows two bands corresponding to phosphorylated PS1 CTF (p-CTF) and one dephosphorylated PS1 CTF (CTF). (B) Densitometry analysis shows the ratio of PS1 p-CTF to CTF. A t test revealed a significant deference between luteolin doses and time points for ratio of PS1 p-CTF to CTF (P<0.005 with n=3 for each condition, but not for ratio of holo PS1 to PS1 NTF (P>0.05 with n=3 for each condition) at each time-point examined. (C) Cultured media were collected for Aβ ELISA. Data corresponds to percentage of Aβ$_{1-40, 42}$ peptides secreted 4 hrs after luteolin treatment relative to control (untreated) as indicated.
Figure 20:
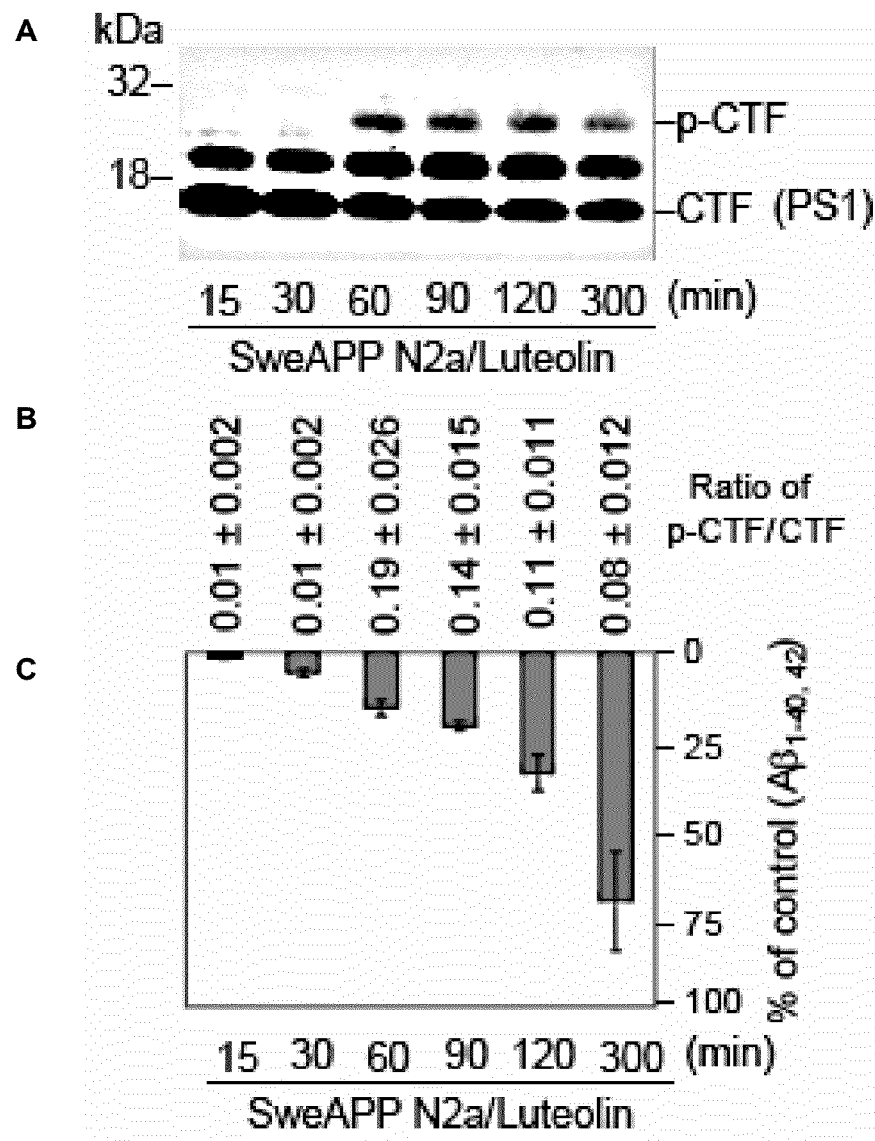
FIG. 20 shows PS1 phosphorylation is associated with luteolin-mediated inhibition of Aβ generation. SweAPP N2a cells were treated with luteolin at 20 μM for various time points as indicated. Cell lysates were prepared from these cells and subjected to Western blot analyses of PS1 C-terminal fragments (CTF). (A) Western blot analysis by anti-PS1 CTF antibody shows two bands corresponding to phosphorylated PS1 CTF (p-CTF) and one dephosphorylated PS1 CTF (CTF). (B) Densitometry analysis shows the ratio of PS1 p-CTF to CTF. A t test revealed a significant deference between luteolin doses and time points for ratio of PS1 p-CTF to CTF (P<0.005 with n=3 for each condition, but not for ratio of holo PS1 to PS1 NTF (P>0.05 with n=3 for each condition) at each time-point examined. (C) Cultured media were collected for Aβ ELISA. Data corresponds to percentage of Aβ$_{1-40, 42}$ peptides secreted 4 hrs after luteolin treatment relative to control (untreated) as indicated.
Figure 21:
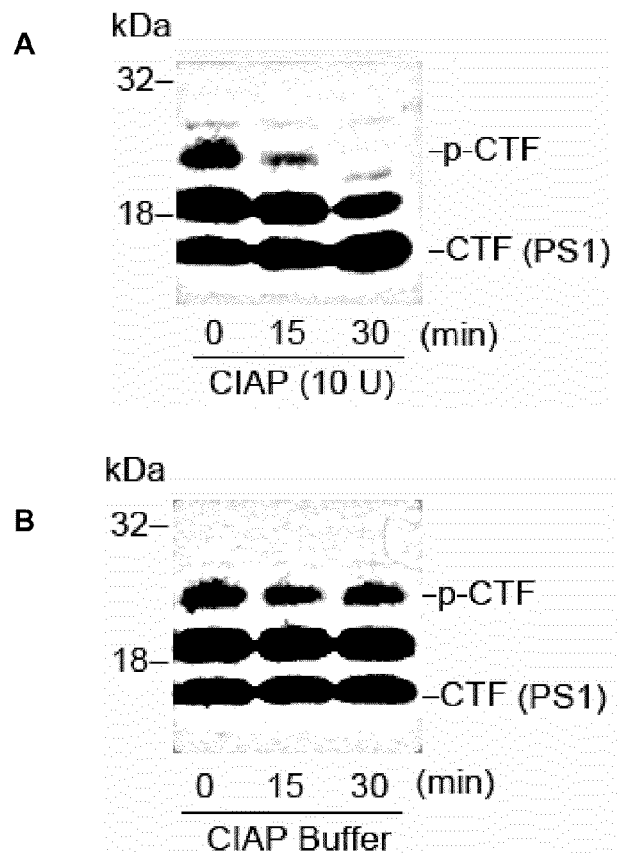
FIG. 21 is a blot depicting PS1 phosphorylation is associated with luteolin-mediated inhibition of Aβ generation. SweAPP N2a cells were treated with luteolin (20 μM) for 30 min. During the luteolin incubation, cell lysates were incubated with (A) calf-intestine alkaline phosphatase (CIAP) for 30 min. or (B) buffer for various time points. Western blot analysis by anti-PS1 CTF antibody confirms two higher molecular weight bands corresponding to phosphorylated isoforms.
Figure 22:
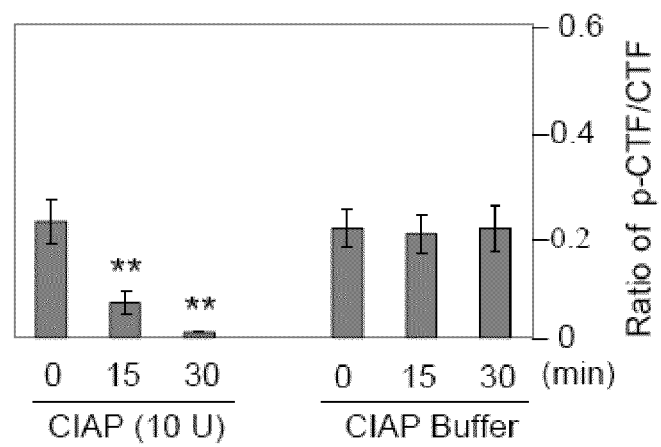
FIG. 22 is a densitometric graph of the blots in FIG. 21, showing the ratio of PS1 p-CTF to CTF.
Figure 23:
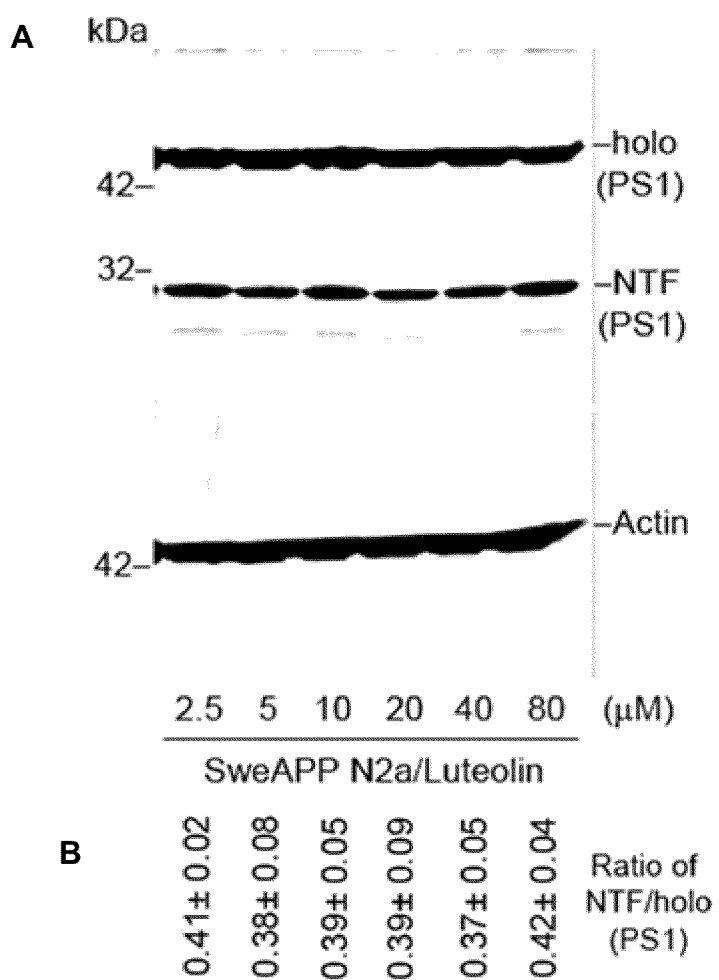
FIG. 23 shows PS1 phosphorylation is associated with luteolin-mediated inhibition of Aβ generation. SweAPP N2a cells were treated with luteolin at a range of doses for 4 hrs. Cell lysates were prepared from these cells and subjected to Western blot analyses of PS1 N-terminal fragment (NTF). Western blot analysis by anti-PS1 CTF antibody shows two bands corresponding to phosphorylated PS1 CTF (p-CTF) and one dephosphorylated PS1 CTF (CTF). (B) A t test of the densitometry analysis revealed a significant deference between luteolin doses and time points for ratio of PS1 p-CTF to CTF (P<0.005 with n=3 for each condition) of FIGS. 19(C) and 20(C), but not for ratio of holo PS1 to PS1 NTF (P>0.05 with n=3 for each condition) at each time-point examined.

Luteolin selectively inactivates GSK-3α isoforms over β isoforms, shown in FIGS. 11 through 18, as luteolin does not inhibit active GSK-3β isoforms at about 2 hrs, depicted in FIGS. 13 and 17, compared to control (data not shown). However, active GSK-3α isoforms are more timely and effectively reduced by luteolin treatment, depicted in FIGS. 13 and 17, indicating luteolin differs from other GSK-3 inhibitors due to its selectivity (including SB-415286). β-catenin also remains unaffected by luteolin treatment, which may imply that this selective GSK-3 inhibition can circumvent the potential toxicity of more general GSK-3 inhibitors (data not shown). Furthermore, there is a clear correlation between increases in inactive and decreases in active GSK-3α, seen in FIGS. 14 and 18, following treatment.

Figure 24:
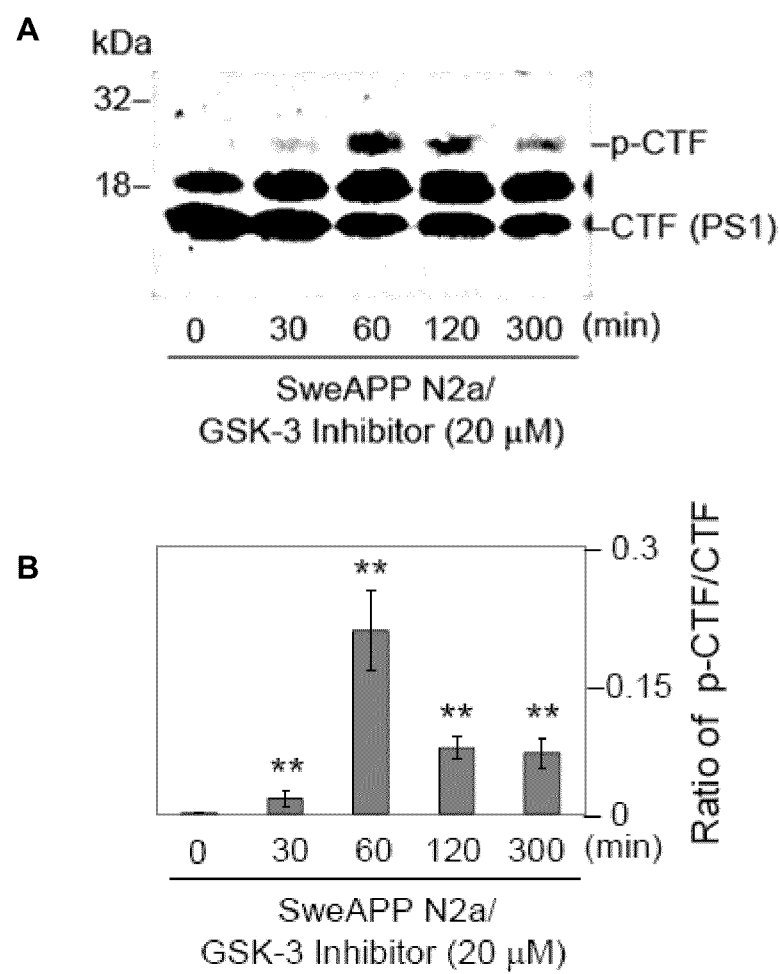
FIG. 24 depicts GSK-3α regulating PS1 phosphorylation. SweAPP N2a cells were treated with a known GSK-3 inhibitor (SB-415286) at 20 μM for various time points. (A) Western blot analysis by anti-PS1 CTF antibody produces consistent PS1-CTF levels among non-treated and luteolin treated cells, whereas PS1-CTF phosphorylation profiles increase sharply at 60 minutes but quickly stabilize at a lower, though elevated, level. (B) Densitometry analysis shows the ratio of PS1 p-CTF to CTF and ratio of holo PS1 to actin as indicated. A t test revealed significant differences between time points for the ratio of PS1 p-CTF to CTF (P<0.001 with n=3 for each condition).
Figure 25:
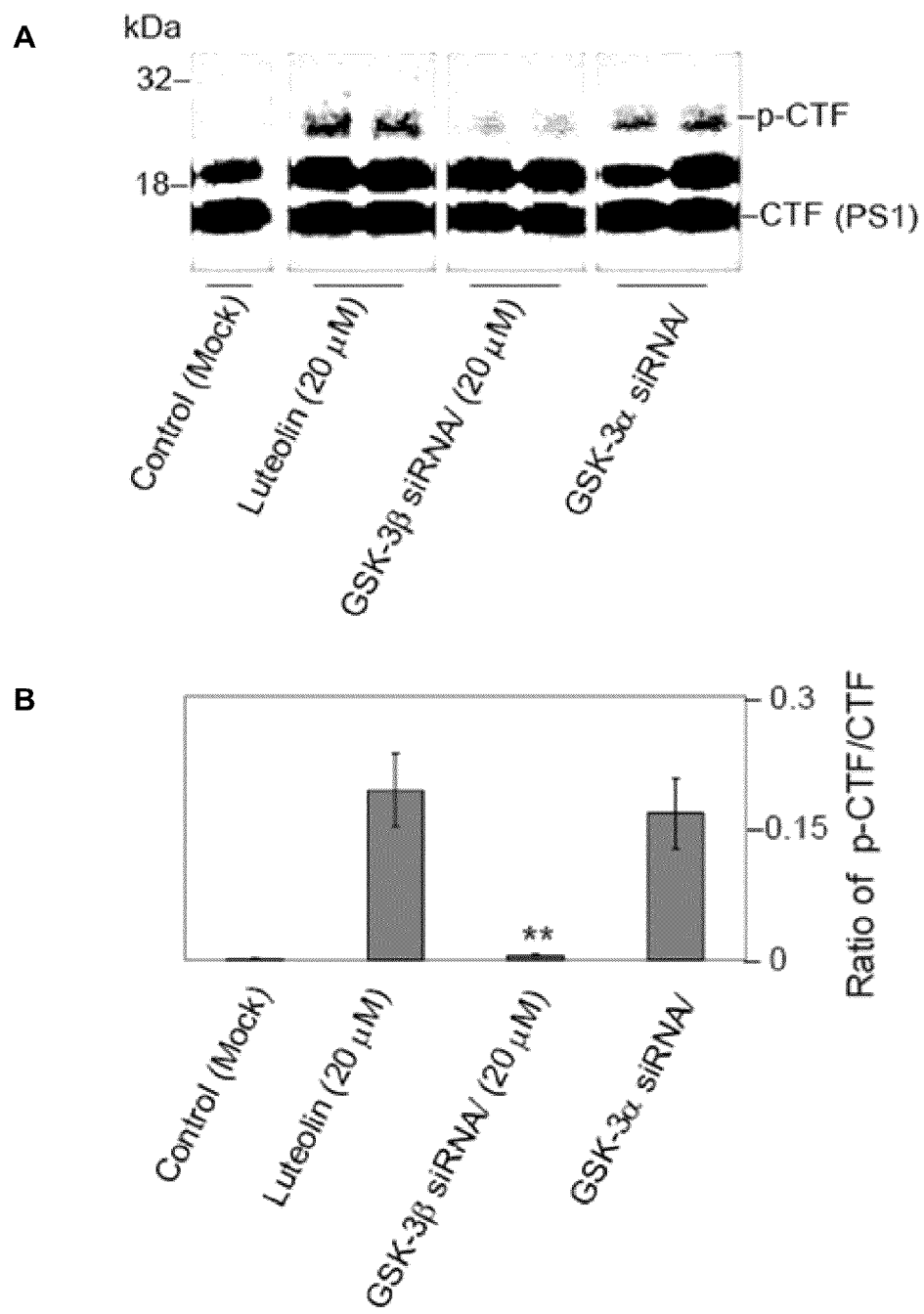
FIG. 25 depicts GSK-3α regulating PS1 phosphorylation. SweAPP N2a cells transfected with siRNA targeting GSK-3α, β, or mock transfected 48 hrs post-transfection. Prior to experiments, siRNA knockdown efficiency >70% for GSK-3α, β was confirmed by Western blot analysis (data not shown). (A) The expression of PS1 C-terminal fragments was analyzed by Western blot in cell lysates of the transfected cells. (B) Densitometric analysis reveals the ratio of PS1 p-CTF to CTF as indicated. A t test revealed significant differences between GSK-3α siRNA-transfected cells and GSK-3β siRNA or control (Mock transfected cells) (P<0.001 with n=4 for each condition) on the ratio of PS1 p-CTF to CTF. In addition, a t test also revealed significant differences between luteolin treated cells and GSK-3β siRNA or control (Mock transfeced cells) (P<0.001 with n=4 for each condition) on the ratio of PS1 p-CTF to CTF.

Luteolin treatment markedly reduces both soluble $Aβ_{1-40, 42}$ isoforms in vivo, seen in FIGS. 24 and 35, illustrating the anti-amyloidogenic agent-effect of luteolin. No changes in insoluble $Aβ_{1-40, 42}$ isoforms were observed, seen in FIGS. 24 and 35; however this result is expected given the age and consequent low plaque burden of these Tg2576 mice. Luteolin potentially reaches its molecular target by passive diffusion through cell membranes, explaining the rapid onset of GSK-3α inhibition observed following luteolin treatment, depicted in FIGS. 11, 12, 15, and 16, and may indicate favorable blood-brain barrier permeability. See FIGS. 26(A) through 35.

Figure 39:
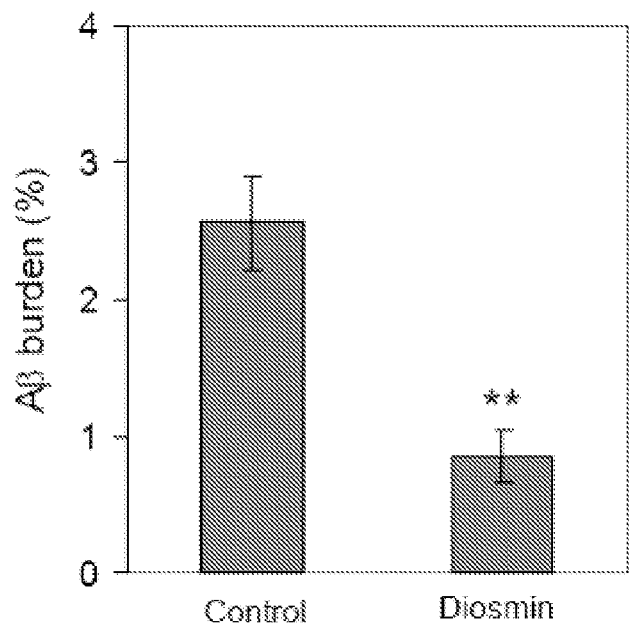
FIG. 39 is a graph of Aβ plaque burden from image analysis of brain sections stained with 4G8 antibody. Data are represented as percentage of immunolabeled area captured (positive pixels divided by total pixels captured). A t test for independent samples revealed significant differences (P<0.001, with n=10 for each condition) between groups.
Figure 40:
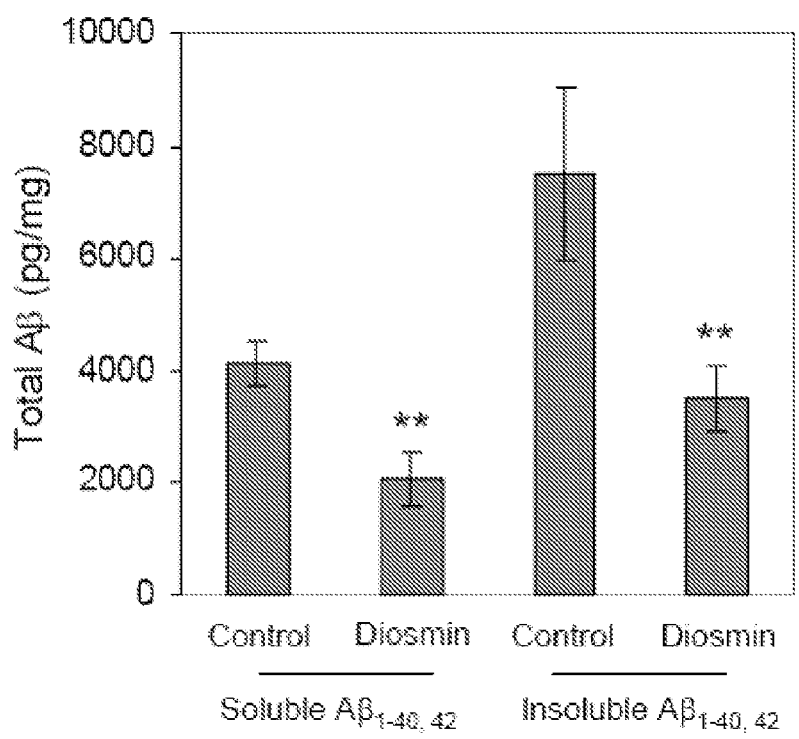
FIG. 40 is a graph of total soluble and insoluble $A\beta_{1-40, 42}$ peptides from homogenates analyzed by ELISA. For Aβ ELISA, data are represented as picograms of peptide present in milligrams of total protein. A t test for independent samples revealed significant differences (P<0.005, with n=10 for each condition) between groups.

It would also appear that diosmetin, via its parent compound diosmin, may possess a favorable blood-brain barrier permeability as Aβ pathology is markedly reduced in treated Tg2576 mice, seen in FIGS. 38, 39, and 40. A micronized nutraceutical formulation of diosmin, under the trade name Daflon, has been successfully used to treat chronic venous disease and hemorrhoids for over a decade in Europe. Recently, improved formulations of diosmin have been marketed in both Europe and the United State for treatment of varicose and spider veins. However, these newer formulations may not actually improve efficacy of diosmin, as diosmetin is likely the active compound responsible for this nutraceutical's therapeutic attributes. At the same time, clinical studies evaluating diosmin and its various formulations have laid the groundwork for future AD clinical trial. Based on the faster metabolic rate of the Tg2576 mice, the dose employed in the oral study would be equivalent to a ~1000 mg of diosmin daily intake in humans.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating an amyloid disease comprising:
   administering to a patient in need thereof and having the amyloid disease a therapeutically effective amount of diosmin;
   wherein the amyloid disease is Alzheimer's disease.

2. The method of claim 1, wherein the flavonoid is administered intravenously, intraarterially, intrathecally, intraperitoneally, intraparenchymally, intracranially, intranigrally, or orally.

3. The method of claim 1, wherein the flavonoid compound is administered at 20 mg/kg.

4. A method of treating a disease characterized by amyloid protein entanglement comprising administering to a patient in need thereof an effective amount of therapeutically effective amount of diosmin;
   wherein the disease is Alzheimer's disease.

5. The method of claim 4, wherein the flavonoid is administered intravenously, intraarterially, intrathecally, intraperitoneally, intraparenchymally, intracranially, intranigrally, or orally.

6. The method of claim 4, wherein the flavonoid compound is administered at 20 mg/kg.

* * * * *